United States Patent
Love et al.

(10) Patent No.: US 11,154,833 B2
(45) Date of Patent: *Oct. 26, 2021

(54) SCREENING ASSAYS AND METHODS

(71) Applicant: President and Fellows of Harvard College, Cambridge, MA (US)

(72) Inventors: J. Christopher Love, Somerville, MA (US); Hidde L. Ploegh, Brookline, MA (US); Jehnna Ronan, Chester, NH (US)

(73) Assignee: President and Fellows of Harvard College, Cambridge, MA (US)

( * ) Notice: Subject to any disclaimer, the term of this patent is extended or adjusted under 35 U.S.C. 154(b) by 62 days.

This patent is subject to a terminal disclaimer.

(21) Appl. No.: 16/170,323

(22) Filed: Oct. 25, 2018

(65) Prior Publication Data

US 2019/0046944 A1 Feb. 14, 2019

Related U.S. Application Data

(60) Continuation of application No. 15/267,977, filed on Sep. 16, 2016, now Pat. No. 10,137,426, which is a
(Continued)

(51) Int. Cl.
*G01N 33/543* (2006.01)
*B01J 19/00* (2006.01)
(Continued)

(52) U.S. Cl.
CPC ....... *B01J 19/0046* (2013.01); *B01L 3/50853* (2013.01); *B82Y 30/00* (2013.01);
(Continued)

(58) Field of Classification Search
CPC ......... B01L 3/50853; B01L 2300/0819; B01L 2300/12; B01L 3/5085; B01L 2300/08;
(Continued)

(56) References Cited

U.S. PATENT DOCUMENTS 4,652,522 A 3/1987 Kennett et al.
4,729,949 A 3/1988 Weinreb et al.
(Continued)

FOREIGN PATENT DOCUMENTS

EP 0258565 A2 3/1988
EP 1566635 A1 8/2005
(Continued)

OTHER PUBLICATIONS

FOR_Muraguchi_Translation_WO2004051266A1—Microwell array chip for detecting antigen-specific lymphocyte—Google Patents Translation (Year: 2004).*
(Continued)

*Primary Examiner* — Rebecca M Giere
(74) *Attorney, Agent, or Firm* — Choate, Hall & Stewart LLP; Brenda Herschbach; William R. Haulbrook

(57) ABSTRACT

Screening assays and methods of performing such assays are provided. In certain examples, the assays and methods may be designed to determine whether or not two or more species can associate with each other. In some examples, the assays and methods may be used to determine if a known antigen binds to an unknown monoclonal antibody.

16 Claims, 26 Drawing Sheets

Specification includes a Sequence Listing.

Related U.S. Application Data continuation of application No. 14/928,607, filed on Oct. 30, 2015, now Pat. No. 9,463,431, which is a continuation of application No. 12/857,508, filed on Aug. 16, 2010, now abandoned, which is a division of application No. 11/523,124, filed on Sep. 18, 2006, now Pat. No. 7,776,553.

(60) Provisional application No. 60/717,976, filed on Sep. 16, 2005.

(51) Int. Cl.
| | | |
|---|---|---|
| *B01L 3/00* | | (2006.01) |
| *G01N 21/64* | | (2006.01) |
| *B82Y 30/00* | | (2011.01) |
| *G01N 33/50* | | (2006.01) |
| *G01N 33/68* | | (2006.01) |
| *G01N 33/577* | | (2006.01) |
| *G01N 33/531* | | (2006.01) |

(52) U.S. Cl.
CPC ........ *G01N 21/6452* (2013.01); *G01N 33/505* (2013.01); *G01N 33/5052* (2013.01); *G01N 33/531* (2013.01); *G01N 33/543* (2013.01); *G01N 33/54366* (2013.01); *G01N 33/577* (2013.01); *G01N 33/6854* (2013.01); *B01J 2219/0074* (2013.01); *B01J 2219/00317* (2013.01); *B01J 2219/00527* (2013.01); *B01J 2219/00585* (2013.01); *B01J 2219/00675* (2013.01); *B01J 2219/00722* (2013.01); *B01J 2219/00725* (2013.01); *B01J 2219/00734* (2013.01); *B01L 2200/025* (2013.01); *B01L 2200/12* (2013.01); *B01L 2300/0819* (2013.01); *B01L 2300/12* (2013.01); *Y10S 436/809* (2013.01); *Y10T 436/24* (2015.01)

(58) Field of Classification Search
CPC ....... B01L 3/502761; B01L 2300/0829; B01L 2300/0854; B01L 2300/0851; B01L 2300/0654; B01L 2300/0896; B01L 2300/0681; B01L 2300/0636; B01L 2300/069; B01L 2300/0822; B01L 2300/0877; B01L 2300/1838; B01L 3/502; B01L 3/502707; B01L 3/508; G01N 21/6452; G01N 21/648; G01N 21/29
See application file for complete search history.

(56) References Cited

U.S. PATENT DOCUMENTS

| | | | |
|---|---|---|---|
| 4,740,467 | A | 4/1988 | Kettman et al. |
| 4,774,177 | A | 9/1988 | Marks |
| 5,124,249 | A | 6/1992 | Khan et al. |
| 5,147,783 | A | 9/1992 | Uda et al. |
| 5,171,664 | A | 12/1992 | Uda et al. |
| 5,494,798 | A | 2/1996 | Gerdt et al. |
| 5,506,121 | A | 4/1996 | Skerra et al. |
| 5,912,176 | A | 6/1999 | Wang |
| 6,180,239 | B1 | 1/2001 | Whitesides et al. |
| 6,197,575 | B1 | 3/2001 | Griffith et al. |
| 6,210,910 | B1 | 4/2001 | Walt et al. |
| 6,377,721 | B1 | 4/2002 | Walt et al. |
| 6,410,252 | B1 | 6/2002 | Lehmann et al. |
| 6,667,158 | B1 | 12/2003 | Bavari et al. |
| 6,767,719 | B1 | 7/2004 | Morin et al. |
| 6,776,094 | B1 | 8/2004 | Whitesides et al. |
| 7,169,578 | B2 | 1/2007 | Wang et al. |
| 7,244,598 | B2 | 7/2007 | Duffy |
| 7,776,553 | B2 | 8/2010 | Love et al. |
| 8,309,035 | B2 | 11/2012 | Chen et al. |
| 8,309,317 | B2 | 11/2012 | Chen et al. |
| 8,772,049 | B2 | 7/2014 | Love et al. |
| 8,835,187 | B2 | 9/2014 | Love et al. |
| 8,835,188 | B2 | 9/2014 | Love et al. |
| 8,865,479 | B2 | 10/2014 | Love et al. |
| 9,463,431 | B2 | 10/2016 | Love et al. |
| 10,137,426 | B2 | 11/2018 | Love et al. |
| 2002/0001576 | A1 | 1/2002 | Sekine et al. |
| 2002/0072116 | A1 | 6/2002 | Bhatia et al. |
| 2002/0137908 | A1 | 9/2002 | Nakamura et al. |
| 2002/0142351 | A1 | 10/2002 | Diamond |
| 2003/0017349 | A1 | 1/2003 | Brown et al. |
| 2003/0030184 | A1 | 2/2003 | Kim et al. |
| 2003/0032002 | A1 | 2/2003 | Wang et al. |
| 2003/0032071 | A1 | 2/2003 | Wang et al. |
| 2003/0113713 | A1 | 6/2003 | Glezer et al. |
| 2003/0113833 | A1 | 6/2003 | Oka et al. |
| 2003/0219816 | A1 | 11/2003 | Solomon et al. |
| 2004/0191924 | A1 | 9/2004 | Hunter et al. |
| 2005/0106641 | A1 | 5/2005 | Kauvar et al. |
| 2005/0112033 | A1 | 5/2005 | Zhang et al. |
| 2005/0136399 | A1 | 6/2005 | Siegel |
| 2005/0220675 | A1 | 10/2005 | Reed et al. |
| 2005/0255491 | A1 | 11/2005 | Lee et al. |
| 2005/0266149 | A1 | 12/2005 | Henderson et al. |
| 2006/0078946 | A1 | 4/2006 | Muraguchi et al. |
| 2006/0134704 | A1 | 6/2006 | Muraguchi et al. |
| 2007/0172887 | A1 | 7/2007 | Takacs et al. |
| 2008/0014631 | A1 | 1/2008 | Muraguchi et al. |
| 2009/0181859 | A1 | 7/2009 | Muraguchi et al. |
| 2011/0046008 | A1 | 2/2011 | Love et al. |
| 2011/0190148 | A1 | 8/2011 | Chen et al. |
| 2011/0195496 | A1 | 8/2011 | Muraguchi et al. |
| 2011/0281745 | A1 | 11/2011 | Love et al. |
| 2011/0281764 | A1 | 11/2011 | Love et al. |
| 2011/0294678 | A1 | 12/2011 | Jin et al. |
| 2012/0015824 | A1 | 1/2012 | Love et al. |
| 2013/0338030 | A1 | 12/2013 | Love et al. |
| 2013/0338047 | A1 | 12/2013 | Love et al. |
| 2014/0011709 | A1 | 1/2014 | Love et al. |
| 2016/0045885 | A1 | 2/2016 | Love et al. |
| 2017/0001166 | A1 | 1/2017 | Love et al. |

FOREIGN PATENT DOCUMENTS

| | | | | |
|---|---|---|---|---|
| EP | 1691196 | A1 | 8/2006 | |
| EP | 2184345 | A1 | 5/2010 | |
| EP | 2365331 | A2 | 9/2011 | |
| EP | 2381255 | A1 | 10/2011 | |
| JP | 63106565 | | 5/1988 | |
| JP | 5240869 | | 9/1993 | |
| JP | 2001504323 | A | 4/2001 | |
| JP | 2002506200 | A | 2/2002 | |
| JP | 2003033177 | A | 2/2003 | |
| WO | WO-9629629 | A2 | 9/1996 | |
| WO | WO-98/10284 | A1 | 3/1998 | |
| WO | WO-2002/055653 | A1 | 7/2002 | |
| WO | WO-2002/078844 | A1 | 10/2002 | |
| WO | WO-03/035824 | A1 | 5/2003 | |
| WO | WO-03080868 | A1 | 10/2003 | |
| WO | WO-2004051266 | A1 * | 6/2004 | ......... G01N 33/5302 |
| WO | WO-2007/035633 | A2 | 3/2007 | |

OTHER PUBLICATIONS

Abbas et al., Cellular and Molecular Immunology, 2nd Ed.: 92-93 (1994).

Abts, H et al., CD20 positive human B lymphocytes separated with the magnetic cell sorter (MACS) can be induced to proliferation and antibody secretion in vitro, Journal of Immunological Methods, 125:19-28 (1989).

Altman, J.D. et al., Phenotypic analysis of antigen-specific T lymphocytes, Science, 274(5284):94-96 (1996).

Carson, D.A. and Freimark, B.D., Human lymphocyte hybridomas and monoclonal antibodies, Advances in Immunology, 38:275-311 (1986).

(56) References Cited

OTHER PUBLICATIONS

Chen, H.J.H. et al., A Novel Micro-Well Array Chip for Liquid Phase Biomaterial Processing and Detection, Sensors and Actuators, 108:193-200 (2003).
Clark et al., Regulation of Human B-Cell Activation and Adhesion, Annual Review Immunology, 9: 97-127 (1991).
Czerkinsky et al., A Solid Phase Enzyme Linked Immunospot (ELISPOT) Assay for Enumeration of Specific Antibody Secreting Cells, Journal of Immunilogical Methods, 65:109-121 (1983).
Falipou et al.. New use of cyanosilane coupling agent for direct binding of antibodies to silica supports. Physicochemical characterization of molecularly bioengineered layers, Bioconj. Chem., 10:346-353 (1999).
Huston, J.S. et al.. Protein engineering of antibody binding sites: recovery of specific activity in an anti-digoxin single-chain Fv analogue produced in *Escherichia coli*, Proc. Natl. Acad. Sci. USA, 85(16):5879-5883 (1988).
International Search Report of PCT/US06/36282, 2 pages (dated Jul. 29, 2008).
Langenkamp et al.. Kinetics of dendritic cell activation: impact on priming of TH1, TH2 and nonpolarized T cells, Nat. Immunol., 1(4):311-316 (2000).
Love, J.C., Declaration as filed in U.S. Appl. No. 15/267,977, 4 pages (dated Nov. 21, 2016).

Michel et al.. Printing meets lithography: soft approaches to high-resolution patterning, IBM J. Res. Dev., 45(5):697-718 (2001).
Muraguchi et al.. Method for Cloning Antigen-Specific Lymphocyte Antigen Receptor Gene, English Translation of Japanese Patent Application No. 2002-346728, (filed Nov. 29, 2002).
Muraguchi et al.. Microwell Array Chip for Detecting Antigen-Specific Lymphocytes and Method for Detecting Antigen-Specific Lymphocytes, English Translation of Japanese Patent Application No. 2002-331031, (filed Nov. 14, 2002).
Ostuni, E. et al., Selective Deposition of Proteins and Cells in Arrays of Microwells, Langmuir, 17:2828-2834 (2001).
Rasmussen, R. et al., T Cell-Dependent Hapten-Specific and Polyclonal B Cell Response Require Release of Interleukin 5, The Journal of Immunology, 140(3):705-712, (1988).
Roome, A.J. and Reading, C.L., The use of Epstein-Barr virus transformation for the production of human monoclonal antibodies, Experimental Biology, 43:35-55 (1984).
Steenbakkers, P.G. et al., A new approach to the generation of human or murine antibody producing hybridomas, J. Immunol. Method, 152:(1)69-77 (1992).
Written Opinion PCT/US06/36282, 6 pages (dated Jul. 29, 2008).
Yamamura, S. et al., Single-Cell microarray for Analyzing Cellular Response, Anal. Chem., 77(24):8050-8056 (2005).

* cited by examiner

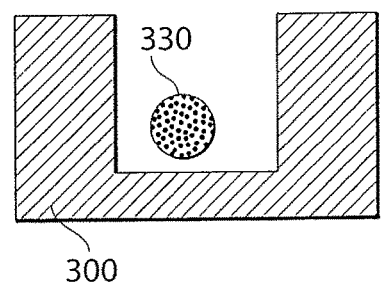
Fig. 3A
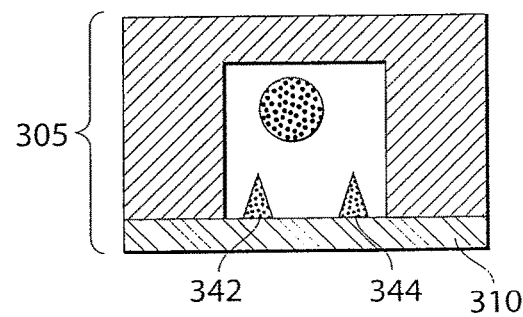
Fig. 3B
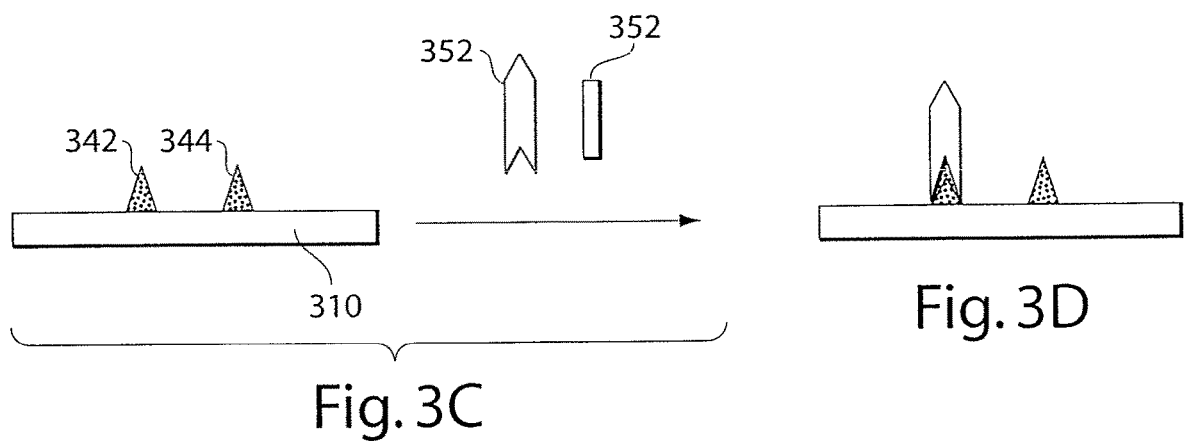
Fig. 3C
Fig. 3D

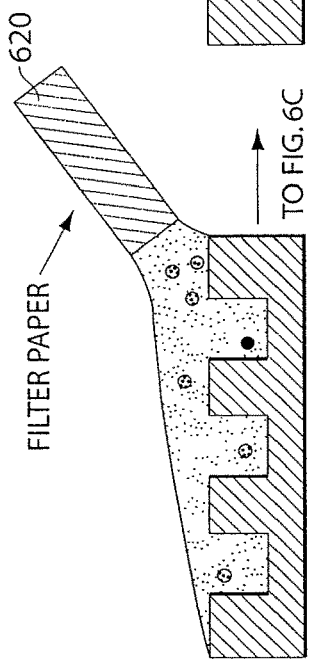
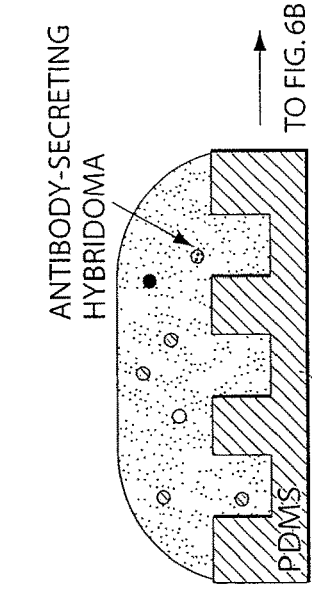
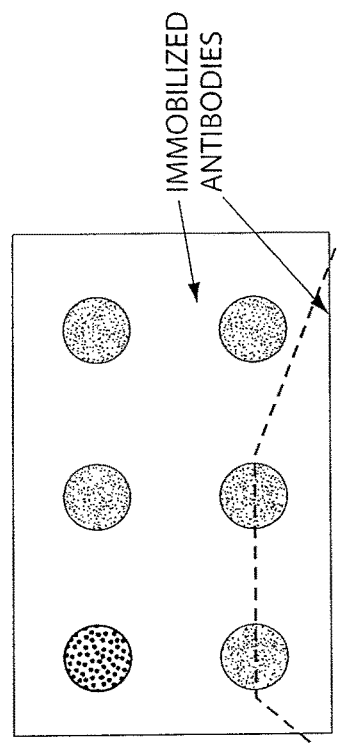
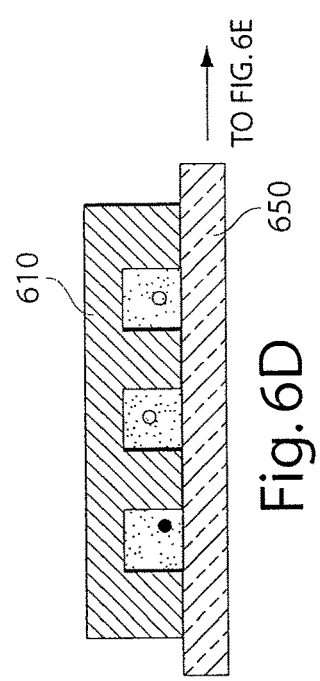

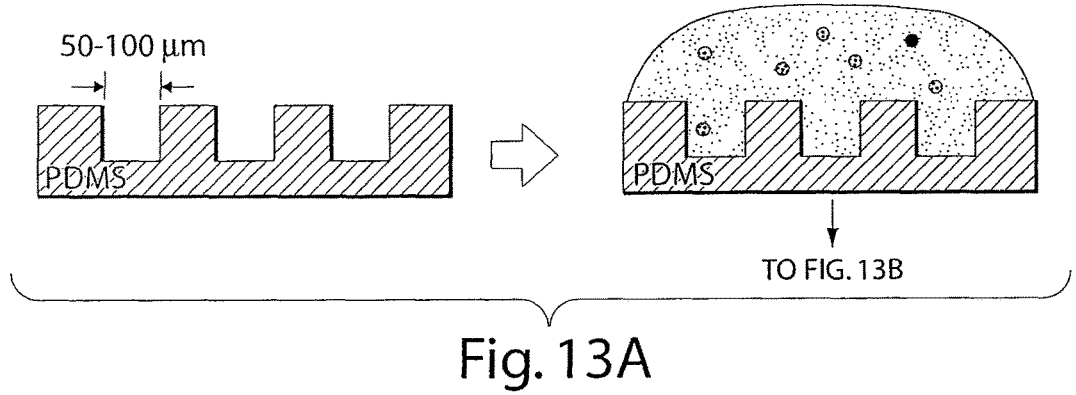
Fig. 13A
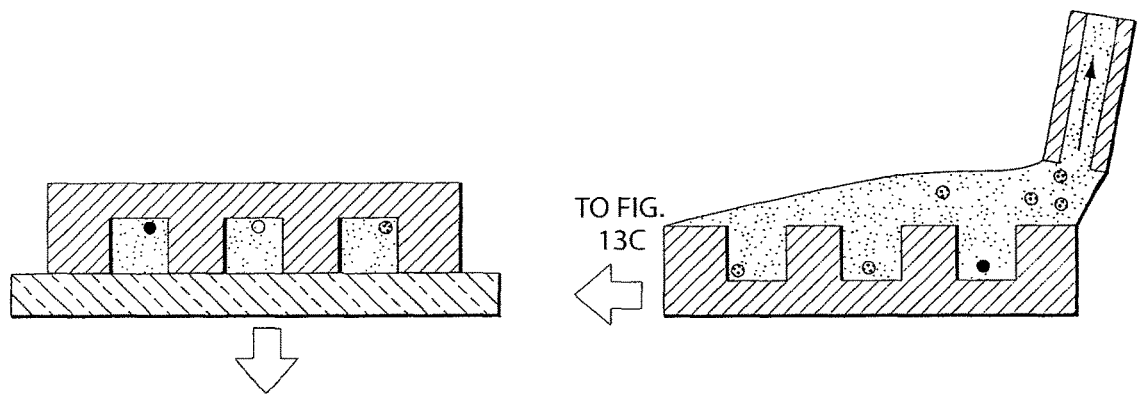
Fig. 13C
Fig. 13B
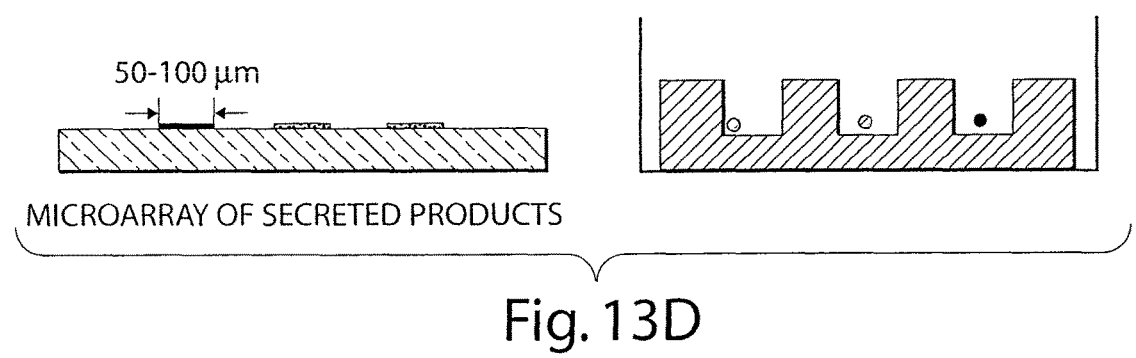
MICROARRAY OF SECRETED PRODUCTS
Fig. 13D

SCREENING ASSAYS AND METHODS

RELATED U.S. APPLICATION

This patent application claims the benefit of U.S. patent application Ser. No. 15/267,977, filed on Sep. 16, 2016, (now U.S. Pat. No. 10,137,426), which is a Continuation of U.S. patent application Ser. No. 14/928,607, filed on Oct. 30, 2015, (now U.S. Pat. No. 9,463,431), which is a Continuation of U.S. patent application Ser. No. 12/857,508, filed on Aug. 16, 2010, which is a Divisional of U.S. patent application Ser. No. 11/523,124, filed Sep. 18, 2006, (now U.S. Pat. No. 7,776,553), which claims priority to U.S. Ser. No. 60/717,976 filed Sep. 16, 2005, the disclosure of each of which is hereby incorporated herein by reference in its entirety.

STATEMENT AS TO FEDERALLY SPONSORED RESEARCH

This invention was funded in part by the U.S. Government under grant numbers NAKFI Nano08 awarded by the National Academy of Sciences and/or grant 5R01AI034893-1 awarded by the National Institutes of Health. The Government has certain rights in the invention.

FIELD OF THE TECHNOLOGY

The invention relates to screening assays and methods to identify secreted products.

BACKGROUND

Assays exist to identify compounds or molecules of interest that may be involved in a disease process or other condition or in treating a disease process or condition. Existing assays have some drawbacks. One significant drawback is the time required to screen for many compounds or molecules. Another drawback is that it may not be possible to recover the compound or molecule post-screening. There remains a need for better screening assays and methods.

SUMMARY

The invention provides a printed microarray of unknown cell-derived products. Each position of the printed array comprises a deposit, which is less than 100 micrometers in diameter, and corresponds to a secretion of a single cell. The deposit is a secreted product such as an antibody, cytokine, chemokine, or inflammatory mediator or another cellular component, e.g., DNA, RNA, or a lipid, which is liberated from an intact cell upon lysis or permeabilization of the cell. Optionally, the printed microarray comprises a capture ligand, e.g., which binds to a single immunoglobin isotype or a chemical capture moiety, e.g., a support derivatized to retain a class of secreted products.

An engraving plate includes a plurality of wells, each of the wells is less than 100 micrometers in diameter and comprises a single cell. Preferably, the number of cells is less than 5 cells. The engraving plate is a gas-permeable conformable composition. The plate has an elastic modulus (Young's Modulus) in the range of 200-2000 Kilopascal (kPa). The composition of the plate is preferably poly (dimethylsiloxane). The wells of the plate contain at least one cell. That cell is an immune cell, an antibody-producing cell, a hybridoma cell, a T cell, or other cell from the blood or a tissue. The function or secretory profile of the cell or cells is unknown. The cell produces a recombinant secreted polypeptide, the polypeptide has an amino acid target sequence for a chemical modification or a recombinant immunoglobulin chain that has an amino acid sequence of an enzyme cleavage site.

This invention also provides a method of screening by disposing a conformable support comprising a plurality of uncharacterized secretory cells on a substrate, e.g., a glass slide, a plastic slide or a bead and exposing a first species comprising an unknown cell-derived, e.g., secreted, product, transferred from the conformable support to the substrate, to a second species to determine if the first species and the second species associate. The second species is a known target ligand, e.g., a defined antigen of a pathogenic organism. For example, the first species is an antibody and the second species is a defined target antigen for which antibody binding is sought.

Another method comprises depositing a suspension of cells onto a moldable slab containing at least one microwell that forms a microwell array that allows the suspension of cells to settle where at least one cell settles into the at least one microwell of the microwell array. The microwell array then contacts a substrate, which is pretreated with a first species. The microwell array is then incubated, for about 1, 5, 10, 20, 30, 40, 50 min but less than 24 hours, and allowing at least one cell to secrete a second species. After incubating, the first species and the second species form an association of the substrate, which is where the microarray is formed. The microarray is then removed from the moldable slab, which still contains cells in the microwells and is placed in a reservoir containing a medium. The cells in the microwells can be maintained in the medium and the microwell array can contact a new substrate and form more than a new microarray, whereby the microwell array can "stamp" more than one microarrays, where about 5 to about 100 microarrays are formed. The association is then detected between the first species and the second species on the microarray.

The second species, which is secreted by the cells, is a monoclonal antibody or a cytokine and the first species is a secondary antibody, wherein a labeled antigen, or fragment thereof, can associate with the monoclonal antibody. Or the first species is an antigen and the second species is a monoclonal antibody, wherein a labeled secondary antibody can associate with the monoclonal antibody. The label is a fluorescent label, a colorimetric label or a radio label. The association on the microarray can be detected with at least one labeled species. The cell is a bacterial cell or a hybridoma, which then is retrieved from the moldable slab if an association occurs between the first species and the second species. The cell is challenged with an antigen prior to disposal of the moldable slab on the substrate. The second species also comprises a catalyst, which is an enzyme and the first species is a potential enzyme substrate or a potential enzyme substrate analog.

The moldable slab is fabricated by soft lithography and replica molding and is of a biocompatible material, which is not toxic and gas permeable. The moldable slab, made of poly(dimethylsiloxane), can compress against the substrate to form a tight, but reversible seal with the substrate. The microwell array comprises a block of wells where a well has a diameter of about 50 µm and a depth of about 50 µm and the wells are separated by about 50 µm or a well has a diameter of about 100 µm and a depth of about 100 µm and the wells are separated by about 100 µm. The wells are sized to retain about 1 nanoliter or less of fluid.

The invention provides a method of screening a monoclonal antibody by contacting a moldable slab with a substrate, which has at least one secondary antibody. The moldable slab contains at least one microwell and at least one hybridoma that secretes a monoclonal antibody in the at least one microwell. The monoclonal antibody is then exposed to at least one antigen to determine if the monoclonal antibody can bind to the antigen. The method is performed in less than about one day or about 6 hours.

A method of screening a monoclonal antibody by contacting a moldable slab to a substrate, where the moldable slab has at least one microwell and at least one hybridoma that secretes a monoclonal antibody in the microwell. The substrate has at least one antigen or at least one secondary antibody on a surface of the substrate. The microarray formed is then used to detect if the monoclonal antibody can bind to the at least one antigen or the at least one antibody on the surface of the substrate. The method of screening the monoclonal antibody is performed in less than about one day or about 6 hours.

A kit is assembled that comprises a substrate, a moldable slab configured to receive the substrate and to provide a fluid tight seal between the moldable slab and the substrate, and instructions for using the conformable support and the substrate to identify species that may associate. The moldable slab or the substrate or both of the kit comprises one or more materials selected from the group consisting of glass, plastic, polystyrene, polycarbonate, poly(dimethylsiloxane), nitrocellulose, poly(vinylidene fluoride), or a metal. The metal is one or more of gold, palladium, platinum, silver, steel or alloys or mixtures thereof. The substrate is a glass slide, a plastic slide or a bead and the moldable slabs contains a microwell array.

A kit comprising a substrate, a moldable slab having a plurality of microwells and configured to receive the substrate and to provide a fluid tight seal between the moldable slab and the substrate, and instructions for using the moldable slab and the substrate to identify species that may associate.

A test apparatus comprising a moldable slab comprising at least one microwell that forms a microwell array that contacts a substrate in a manner to provide a fluid tight seal between the moldable slab and the substrate. The apparatus puts one species, generally a cell, in at least one well of the microwell array and the microwells of the moldable slab are sized and arranged to retain about one nanoliter or less of fluid volume. The analytical methods described herein offer numerous advantages over prior methods, including time-saving and cost effectiveness.

All publications, patent applications, patents, and other references mentioned herein are incorporated by reference in their entirety. In addition, the materials, methods, and examples are illustrative only and not intended to be limiting.

BRIEF DESCRIPTION OF THE FIGURES

FIGS. 3A-3D are schematics of a method for detecting association of two species, in accordance with certain examples.

FIGS. 6A-6E are schematics of a method for immobilizing antibodies on a substrate, in accordance with certain examples.

FIGS. 13A-D is a schematic diagram depicting method for preparation of engraved arrays of secreted products from a mixture of cells.

Figure 1A:
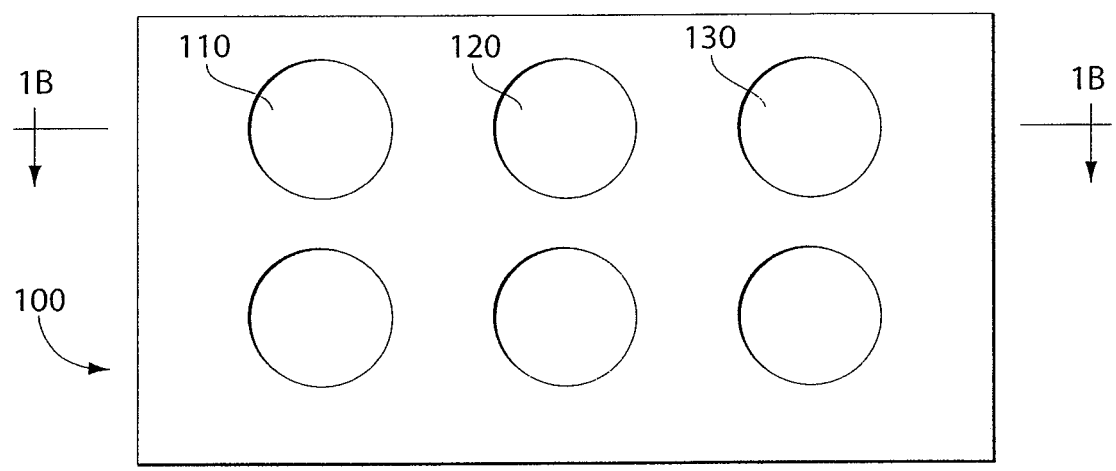
FIG. 1A is a top view and FIG. 1B is a cross-section of a schematic along section line 1B-1B of a moldable slab, in accordance with certain examples.

It will be recognized by the person of ordinary skill in the art, given the benefit of this disclosure, that the examples shown in the figures are not necessarily drawn to scale. Certain features or components may have been enlarged, reduced or distorted to facilitate a better understanding of the illustrative aspects and examples disclosed herein. In addition, the use of shading, patterns, dashes and the like in the figures is not intended to imply or mean any particular material or orientation unless otherwise clear from the context.

DETAILED DESCRIPTION

The methods of the invention allow identification and characterization of previously unknown or undefined cell-derived compositions. The compositions are secreted such as antibodies or cytokines or compositions that are released upon lysis or permeabilization of the cell such as cytoplasmic, nuclear, or cell membrane components. Any cellular composition including biopolmers, e.g., DNA and RNA, as well as lipids and glycolipida, is captured by this method provided that the solid support (substrate) is appropriately functionalized (e.g., poly dT nucleotides for RNA). In addition to immune cells, other eukaryotic cells are interrogated. For example, single cell suspensions from normal or cancerous tissue of tissue type, e.g., heart, brain, liver, prostate, breast, or colon. The systems are also useful to characterize whole cells and secreted products from their cell types (bacteria, yeast, small parasites (malaria)).

In addition to analysis of secreted cell-derived products, the method encompasses characterization of the cells remaining in the wells after the capture of the secreted products (e.g., by immunofluoresence, genetic sequencing). In conjunction with identification and characterization of secreted products, the cells in corresponding wells are retrieved and matched with the materials secreted.

The methods, apparatus and kits disclosed herein are used to identify antibodies and other cell secreted products. Hybridomas may be identified using these methods. Hybridomas are made using known methods, for example, a mouse is immunized with an antigen or a plurality of antigens. The spleen of the mouse is removed and broken up to form a suspension. The suspended spleen cells are fused with mouse myeloma cells, e.g., in polyethylene glycol. The cells are then cultured over several days in media containing hypoxanthine, aminopterin and thymidine (HAT media) such that any unfused spleen cells die. Unfused myeloma cells also are killed in the HAT media because they lack the enzyme hypoxanthine ribosyl transferase (HPRT) and thus cannot produce inosine from hypoxanthine, and the aminopterin prevents the myeloma cells from using an alternative pathway to produce inosine from thymidine. Because inosine is a precursor to many nucleic acid pyrimidines, the myeloma cells die because they are unable to produce nucleic acids. In contrast, the hybridomas have the HPRT and can use the hypoxanthine and the thymidine in the HAT media to produce nucleic acids.

Using the methods, apparatus and kits disclosed herein, a single, or a few hybridomas are placed in a microwell of a moldable slab and are allowed to produce monoclonal antibodies for a few hours, e.g., 4-8 hours. Secreted monoclonal antibodies are immobilized on a substrate and exposed to known antigen(s) to determine which monoclonal antibodies binds to the known antigen. Results lead to a rapid high-throughput screening of hybridoma cells that product antibodies against specific antigens and also allows for the identification and expansion of cells producing monoclonal antibodies.

Another application for the method, apparatus and kits disclosed herein is to identify personalized antibodies raised against tissue samples from an individual. For example, the methods, apparatus and kits disclosed herein may be used to raise antibodies against a tumor in an individual. A sample or biopsy of the individual's tumor may be taken and injected into a mouse. After several weeks, the mouse's spleen cells may be removed and monoclonal antibodies may be identified. Production of such monoclonal antibodies may provide for treatment of the individual's tumor by injection or administration of the produced monoclonal antibodies, e.g., site-specific delivery of the monoclonal antibodies. Fully humanized antibodies containing a human constant region (Fc) would be ideal for this application.

Another application for the method, apparatus and kits disclosed herein is to determine the efficacy of an immune response related to a particular immunotherapy such as a vaccine. For example, the number of lymphocytes secreting specific molecules indicative of proliferation (e.g., TNF-alpha, IL-1, IgE) and the overall output levels of these markers from individual cells may be assayed. The assay may require antibodies against each secreted factor immobilized on the substrate to capture molecules produced by individual cells and a second specific antibody with a fluorescent marker to screen for the amount of each marker captured on the substrate. This assay produces a new type of personalized medicine for evaluating the responsiveness of individuals to selected immunotherapies.

The advent of antimicrobial drugs and vaccines using inactivated or attenuated microorganisms has had a remarkable impact on the overall health of the world population in the last 150 years, especially in first-world countries. In the present era, however, there has been a resurgence of infectious diseases thought to be under control or eradicated. New outbreaks of lethal infectious diseases that have been suppressed in recent times by the administration of antibiotics or first generation vaccines (*staphylococcus*, rubella, mumps) underscore this observation. Evolutionary pressure applied to various microorganisms by the use of vaccines and antimicrobial drugs has resulted in increasing numbers of strains resistant to current therapeutics. These factors combined with both existing and potential epidemic diseases—HIV, malaria, influenza—for which treatments are limited, if available at all, suggest a need for new therapies—either vaccines or drugs.

Two current strategies for developing new therapies for infectious diseases are: 1) rational design of vaccines, and 2) generation of therapeutic monoclonal antibodies (mAb). The knowledge of the genomes for common pathogens, and the advent of computational tools for mining these data, has enabled a more rational approach for determining immunogenic factors than empirical data from inactivated materials. Although polyclonal sera containing antibodies have been used clinically for passive immunization since the late 1800s, their use in modern medicine has been limited by the advent of antimicrobial drugs. The development of hybridomas and related technologies in the 1970s and 1980s has led to monoclonal therapies, but economic and political suasions have focused these treatments largely on cancer and autoimmune disorders. The threat of bioterrorism has renewed interest in identifying antibodies against potential biological agents, e.g., anthrax.

At least two factors continue to hinder progress in identifying surface-expressed, immunogenic epitopes on pathogens and subsequently, new therapies. First, genomic analysis has yielded some leads for formulating new vaccines, but it can not predict other factors that can enhance (or mask) the immunogenicity of an epitope—post-translational modifications, conformational variations, non-proteinaceous materials, or genetic variation among serotypes. Second, for therapies based on neutralizing antibodies, it is likely that single mAbs for infectious diseases will be insufficient; a cocktail of mAbs recognizing a range of epitopes should be more effective than a single mAb. Libraries of suitable mAbs from which to create such cocktails are small or non-existent. Thus, new tools for the rapid identification of antigens that evoke robust and protective immune responses for a large number of infectious agents would greatly assist in the design of vaccines against epidemic infectious diseases (malaria, HIV, influenza) and prophylactic treatments for others (small pox, anthrax). This screening technology enables high-throughput and rapid analysis of large polyclonal populations of immortalized B cells (>100,000 cells in <12 h) to identify clones producing antibodies reactive against the surface epitopes of a pathogen.

There is growing evidence that common phenotypic markers (e.g., CD4+) can encompass a number of subsets of cells with diverse functions, indicated by the types of cytokines secreted. A simple analytical tool that provides information about both phenotypic markers and secreted factors for individual primary cells (without extended ex vivo culturing) facilitates studies in cell biology, especially immunobiology. The methods disclosed make it possible to retrieve the cells for subsequent culture or genetic analysis, applications include i) profiling immunological responses to administered vaccines, allergic reactions, or foreign pathogens, and ii) extending understanding of the cell biology of cancers and autoimmune disorders.

Also, the disclosed method, apparatus and kits is a simple analytical assay for individual primary cells that allows both determination of their phenotypes (expressed surface or intracellular proteins) and direct measurement of their functional behaviors (secreted cytokines, antibodies, growth factors). More specifically, the technology rapidly correlates surface-displayed phenotypes with functional secretory behaviors of individual primary cells, preferably without extended culture or other manipulations that could modify the expression of markers or the behavior. Application of the methods, apparatus and kits make it possible to have a platform for the systematic analysis of an immune response to various diseases, allergies, and treatments (e.g., vaccines) or a systematic analysis of immune responses for individuals to various diseases using limited sizes of samples, and should facilitate the transition of clinical medicine towards predictive, personalized healthcare.

Antibodies are ubiquitous reagents in biology for applications that range from basic biochemistry to clinical diagnostics. They are commonly immobilized on surfaces to retrieve other biopolymers from a surrounding solution (sera, culture supernatant). Examples of supports used include beads/resins, microarrays, and nanoparticles. The most frequent methods for immobilizing antibodies are i) physical adsorption onto a hydrophobic substrate, ii) covalent attachment at reactive sites on the protein, or iii) non-covalent interactions between an immobilized receptor (streptavidin, protein A or G, anti-Ig) and an antibody or its derivative multiply decorated with ligands. These strategies do not induce a specific orientation on every antibody immobilized—for example, with the binding region positioned away from the underlying surface. Though random orientation of a protein on surfaces may be sufficient in many assays designed to determine unknown protein-protein interactions, the development of miniaturized biological assays that incorporate micro- and nanoscale components (with limited surface areas) motivates the need for new strategies to attach antibodies (and other proteins) on surfaces that preserve function in high-density. The sensitivity of detection and the yield of capture depend on the number of binding sites available at the interface between the supporting surface and the surrounding solution. Two key parameters influencing this value are: i) the density of molecules and ii) the accessibility of the binding region on the immobilized molecule to other molecules at the interface. Orientation of an immobilized molecule on the surface is, therefore, important for improving accessibility.

The miniaturization of microarrays on planar surfaces can improve the density of information available in a single experiment, and the incorporation of nanoparticles in biological assays can improve the sensitivity of diagnostics. Both applications require functional organic surfaces capable of binding specific molecules from a surrounding solution, but in both instances, the available surface area per feature or particle is limited. This characteristic suggests that the overall limits of detection afforded by these methods will depend on the number of functional receptors presented at the interface between the solid support and the surrounding environment. Although antibodies are used routinely in immunochemical assays for detecting specific analytes, most techniques for immobilizing them on surfaces do not favor a particular orientation of the molecules. This example outlines an approach for engineering full-length antibodies to carry a specific chemical functionality at the C-terminus of the heavy chains of the immunoglobulin. The addition of a short peptide sequence recognized by an enzyme, BirA ligase from *Escherichia coli*, makes it possible to incorporate an unnatural analog of biotin containing a ketone to the antibody. Reaction of this moiety with an organic surface designed to resist non-specific adhesion of other proteins improves the orientation of the modified antibodies attached to the surface. This general approach extends to other proteins of interest (fragments of antibodies, recombinant enzymes).

Examples of the technology disclosed herein may be used to identify unknown species disposed on a substrate that can associate with a known species. For examples, the methods disclosed herein are used to identify an antibody that binds to or interacts with a desired target antigen. The exact nature of the assays depends, for example, on the selected species, the selected slab or substrate and the information desired from the assay. Certain embodiments of the technology disclosed herein provides significant advantages including, for example, (1) a single array of microwells can contain greater than 625 wells per square inch compared to about 1 well per square inch for a conventional 96-well plate; (2) the dilution of a single cell per well makes it possible to identify cells producing antigen-specific antibodies in a single screen compared to iterative testing required for assays using conventional methods, such as a 96- or 384-well plates; (3) the limited volume of the microwells (about 1 nanoliter or less) permits sufficient concentrations (e.g., about 1 µM) of antibody to be reached within a few hours instead of 5-7 days; (4) an assay for positive antibodies may be integrated into a method and does not require any additional manipulations to array or test the secreted antibodies for specificity; and (5) the screening methods, apparatus and kits can be multiplexed to screen simultaneously for many different cells producing antibodies against different antigens.

In accordance with certain examples, the methods, apparatus and kits disclosed herein may be used in determining whether or not two species associate. As used herein, the term "associate" refers to interactions such as binding, adsorption, ionic attraction or some other type of interaction between the two species. In some examples, species that associate preferably bind to each other with an association constant of at least about $10^9$ $M^{-1}$ or larger. Species which bind to each other with such association constants allow for easy distinction between species that associate and those that do not associate.

In accordance with certain examples, a moldable slab may be used in the methods and kits described herein. As used herein "moldable slab" refers to an apparatus which can flex, move or distort, at least in one dimension, when placed in contact with a substrate. For example, in certain configurations the moldable slab may include a material, e.g., an elastomeric material, such that as the moldable slab is placed in contact with a substrate, a substantially fluid tight seal may be formed between the moldable slab and the substrate to retard or to prevent any fluid in the moldable slab from escaping or leaking.

Protocols for identifying cells from a single colony that serve as sources of monoclonal antibodies rely on limited dilution of candidate cells into microtiter plates. The cells are diluted into 96-well plates or 384-well plates, and expanded for 5-7 days. At that time, aliquots of the media from each well may be tested to identify positive wells producing the desired antibody. For example, an immunoassay such as enzyme-linked immunosorbant assay (ELISA) may be used to identify positive wells producing the desired antibody. The contents of the positive well are then diluted again into a microtiter plate and the process is repeated until the entire plate is derived from a single colony. This serial process typically requires 2-3 months to complete and usually allows only about 1000 different types of cells to be screened for the desired functionality (e.g., producing a specific antibody).

Two factors determine the time required to isolate a single monoclonal hybridoma by this method. First, the sensitivity of the assay used to detect antibodies of interest sets the frequency at which cloned cells can be tested for specificity—for example, sufficient concentrations of antibodies that can be detected by enzyme-linked immunosorbant assays (ELISA) are achieved seven to ten days after seeding individual cells into a microtiter plate. Second, the total number of manipulations limits the number of clones that can be screened efficiently in any single round of selection (10-100 plates/screen).

Two alternatives for sorting cells into microtiter plates at limiting dilutions include picking clones from semi-solid media, and fluorescence-activated cell sorting (FACS). Cells plated in agar or other hydrogels are challenged to survive and grow slowly, and the correlation between cells that stain positive in FACS and those that readily secrete products is not straightforward. Both methods have improved the efficiency of screening by serial dilution, but the resulting cultures usually require additional independent testing by ELISA or equivalent methods to verify secretion and specificity. Other methods have been developed for the analysis of individual cells in large numbers, such as microfluidic devices, cell-based microarrays, ELISPOT and hemolytic plaque assays, but these methods do not allow both high-throughput analysis of a secreted product and the recovery of living cells for clonal expansion.

Generally, arrays of antibodies with known specificities are used to detect the presence or absence of specific analytes in an unknown mixture, which is used as an analytical tool for detecting known antigens with known antibodies; it is not designed for discovering new types of antibodies. Arrays of microwells are also used for screening for hybridomas producing antigen-specific antibodies but then are subsequently, not in parallel, screened by traditional immunoassays (flow cytometry, ELISA) for antigen specificity.

In contrast, examples of the methods, apparatus and kits described herein may use a moldable array of microwells or chambers (e.g., ~50-100 microns in diameter) to retain one (or a few) cells in each microwell. The array is placed in physical contact with a substrate in such a manner that the microwells become closed containers or a test apparatus. Incubation of this system allows the cells to produce products, such as, antibodies, cytokines and other secreted products, that are then immobilized on the substrate in the regions contacted by the microwells. In this manner, a microarray of the cellular products from each microwell is produced. After incubation of the system for a suitable time, e.g., 1, 5, 30, 40, 50 minutes to a few hours, the microwell array is removed from the substrate, and the immobilized cellular products on the substrate, the microarray or microengraving, may be screened with a known species to determine whether or not the immobilized cellular product(s) associate with the known species. The method disclosed herein represents a novel approach by combining detection of species present in an unknown mixture and, in a parallel and efficient manner, screening for hybridomas producing antigen-specific antibodies. Additional uses for screening non-cellular products using the methods, apparatus and kits are also described.

The soft lithographic technique is used to microengrave a dense array of microwells (0.1-1 nL each) containing individual cells to print a corresponding array of the molecules secreted by each cell. The cells remain in culture in a microwell after the engraving, and the microarrays are interrogated in a manner similar to commercial microarrays of proteins or antibodies—for example, by use of fluorescently labeled reagents and laser-based fluorescence scanners. This method, therefore, enables rapid identification of those cells that exhibit desired properties, such as secretion of an antigen-specific antibody, and their subsequent recovery from individual wells for clonal expansion.

Figure 1B:
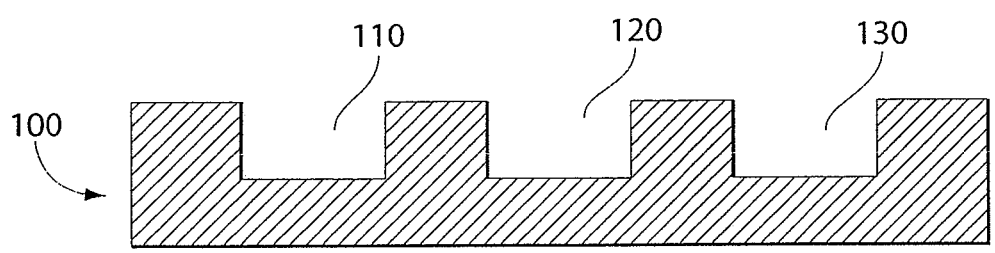

Referring to FIGS. 1A and 1B, a top view of a moldable slab 100 is shown. The moldable slab 100 comprises a plurality of microwells or chambers, such as microwells 110, 120 and 130. In the illustration shown in FIG. 1A, each of the microwells is shown as having substantially the same cross-sectional shape. For example and also referring to FIG. 1B, which shows a cross-section through line 1B-1B in FIG. 1A, the cross-section of the moldable slab 100 shows microwells 110, 120 and 130 as being circular when viewed from the top and generally cylindrical when viewed from a side. The exact number, dimensions, shape and the like of each microwell of the moldable stab 100 may vary. For example, when viewed from the top, the cross-section of each microwell may be circular, square, elliptical, toroidal, rhomboid or other selected shape. In addition, any particular microwell of the moldable slab may be a different shape than another microwell in the moldable slab.

In certain configurations, each microwell of the moldable slab may be sized and arranged to retain or to hold a single cell or a few cells (e.g., 3-5 cells), such as a bacterial cell, a hybridoma or other selected cell. In some examples, the diameter of each microwell of the moldable slab may vary from about 10 microns to about 100 microns, more particularly, about 25 microns to about 100 microns, e.g., about 50-100 microns. Additionally each microwell is separated from another by a length similar to the depth and/or height. The size of any selected microwell may vary depending on the size of the cell, or cells, to be retained by the microwell. In certain examples, the microwell is sized to be large enough so that the cell may remain viable but is not so large that any products produced by the cell will be diluted by a large fluid volume. For example, the volume of each microwell of the moldable slab is large enough to retain a cell and to provide a buffer, nutrients, etc. to keep the cell alive, but the volume of the microwell is not so large that any desired screening products will be diluted by solvent or buffer to a non-detectable level. In certain configurations, the volume of the microwell varies from about 1 picoliter to about 100 nanoliters, more particularly about 10 picoliters to about 10 nanoliters, e.g., about 100 picoliters to about 1 nanoliter.

The exact number of the wells or chambers in the moldable slab may vary. In some examples, the moldable slab may include a single large microwell where a single species may be screened. For example, a moldable slab may include a single type of cell, catalyst or other selected species that may be screened. In configurations where the moldable slab is configured as an array, the number of individual microwells may vary from about 24, 48, 96, 384, 1024, 2048, 5096 or more or any value in between these illustrative values. As material in the moldable slab is transferred to the substrate, an array of disposed material forms on the substrate which reflects the material present in the microwell or microwells of the moldable slab. One or more of the microwells in the moldable slab may be blocked or prevented from transferring material to the substrate using an insert or device placed between a particular microwell in the moldable slab and the substrate. This feature provides for selective disposition of arrays of material on a substrate.

The moldable slab may be configured in a variety of manners. For example, the moldable slab is configured as a plate comprising one or more microwells. The moldable slab may also be configured as a bead comprising one or more microwells or a bead configured to retain material on its surface. Any particular configuration for a moldable slab may be used provided that material on the moldable slab, or products produced by material on the moldable slab, may be transferred, at least to some extent, to a substrate.

Figure 1C:
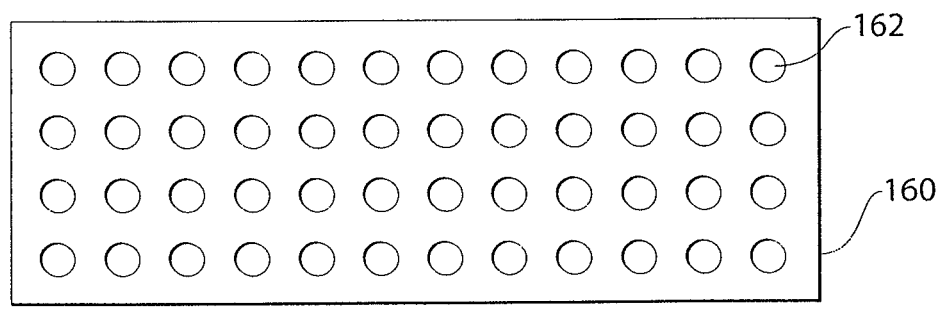
FIG. 1C is a top view of an insert and FIG. 1D is a side view of an insert in contact with a moldable slab, in accordance with certain examples.
Figure 1D:
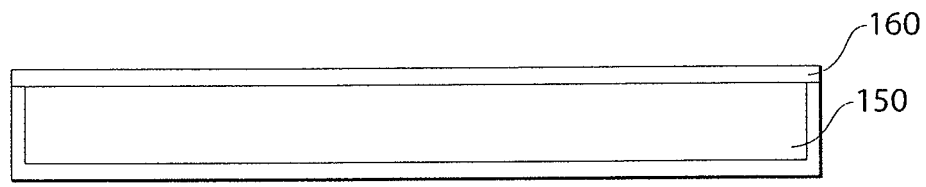

The moldable slab is configured to receive an insert comprising one or more openings. In certain examples, the insert comprises a plurality of openings. Referring now to FIGS. 1C and 1D, a moldable slab 150 comprises an insert 160 which may be disposed on top of the moldable slab 150. The insert 160 may be permanently fixed or may be removable. In this illustration, the insert 160 comprises a plurality of openings, such as opening 162. As the moldable slab 150 is brought into contact with a substrate, the openings in the insert 160 allow for transfer of material from the moldable slab 150 to certain areas on the substrate. As material is transferred from the moldable slab 150 to the substrate through openings in the insert 160, an array is formed on the substrate which reflects the number of openings, and spacing of the openings, of the insert 160. This configuration permits the moldable slab 150 to take the form of a single large microwell which may be used to hold material such as, for example, a hybridoma, a bacterial cell and the like. The moldable slab contains one or more inserts and the insert is produced by using the same or similar materials that are used to produce the moldable slab.

The material or materials used to produce the moldable slab include polymeric and metallic compositions. In certain examples, the moldable slab may be made from two or more materials, only one of which may impart the moldable properties to the slab. In other examples, two or more materials which are elastomeric may be used. Illustrative materials include, but are not limited to, glass, plastic (including both rigid and soft materials), polystyrene, polycarbonate, poly(dimethylsiloxane) (PDMS), nitrocellulose, poly(vinylidene fluoride) (PVDF), metals such as gold, palladium, platinum, silver and alloys thereof, steel and mixtures of any of these materials. The rigidity of some materials, such as polystyrene, would not allow for conformal contact, and thus sealing, of the microwells against a substrate for testing the specificity of the antibodies produced in a parallel. PDMS, however, is a suitable material for this technique because it is not toxic, it is gas permeable, and it is easily compressed to form a tight, but reversible, seal with a rigid substrate.

In other examples, sols or gels, e.g., agar, a hydrogel, matrigel, etc. may be used in the moldable slab. In some examples, the material to be assayed, or cells which secrete a material to be assayed, may be embedded, impregnated in or injected into the moldable slab. For example, a monolayer of cells is cultured on the moldable slab. In some examples, cells are embedded in a hydrogel which is used to produce, or is coated on, the moldable slab. Additional materials suitable for use in the moldable slabs will be readily selected by the person of ordinary skill in the art, given the benefit of this disclosure.

The moldable slab may include additives, fillers, insulators, growth factors and the like. For example, the moldable slab may include one or more materials which act as an insulator to assist in keeping a substantially constant temperature for the materials, e.g., cells, in the moldable slab. The moldable slab may also include antibiotics or other compounds which can reduce or prevent growth of unwanted organisms such as, for example, bacteria or fungus. Such additional materials may be included in the moldable slab, coated on the moldable slab, e.g., only in the microwells or on the entire moldable slab, or may otherwise be impregnated in the moldable slab to provide a desired result.

The moldable slab may be cast in a mold using suitable materials described above. Photolithographic and replica molding techniques may be used. The material is coated on a master mold, vapor deposed on a master mold or added onto or in a master mold to provide a moldable slab comprising a desired number of chambers. In some examples, a moldable slab configured as an array is produced using photolithography and replica molding, from monolithic slabs of poly(dimethylsiloxane) (PDMS). For example, a layer of a photoresist is patterned on a suitable substrate, such as a 3 inch silicon wafer, to produce a master with a positive relief pattern of the moldable slab. A suitable material (e.g., PDMS) is cast onto the master, cured and peeled away to provide the moldable slab. In other examples, a moldable slab is produced by casting a material and using a press, plate, punch, air or the like to provide depressions in the surface of the cast material prior to curing or hardening of the cast material. Generally, at least 50 replicas are created from a single mold with minimal wear. Additional methods for producing moldable slabs suitable for use with the methods, apparatus and kits disclosed herein will be readily selected by the person of ordinary skill in the art, given the benefit of this disclosure. Illustrative methods for producing moldable slabs are described in more detail in U.S. Pat. Nos. 6,180,239 and 6,776,094, the entire disclosure of each of which is hereby incorporated herein by reference in its entirety.

A substrate may be used with the moldable slab to provide a test apparatus. The configuration of the substrate may vary and typically the substrate is selected such that it can "mate" with the moldable slab to provide a substantially fluid tight test apparatus. The ability of the moldable slab to flex, distort, bend, conform, etc. to a surface of the substrate assists in providing a substantially fluid tight test apparatus. In certain examples, the substrate may be a solid substrate, such as a glass or plastic slide, which may be placed on or in contact with the moldable slab. Generally, the array was designed to fit within the boundaries of a 1"×3" glass slide—a common format for microarray readers; variations in shape and spacing of individual wells were used to encode their specific location within the array.

Figure 2A:
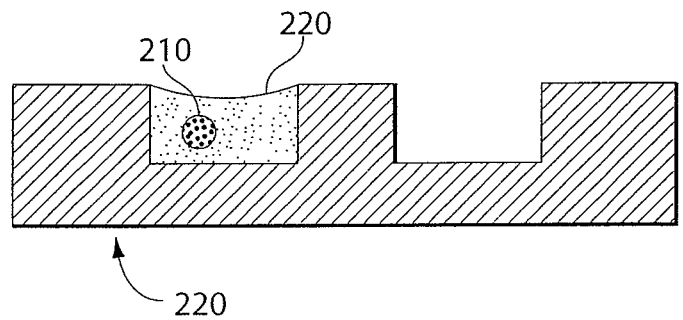
FIGS. 2A-2D are schematics of a method for transferring material secreted by a cell to a substrate, in accordance with certain examples.
Figure 2B:
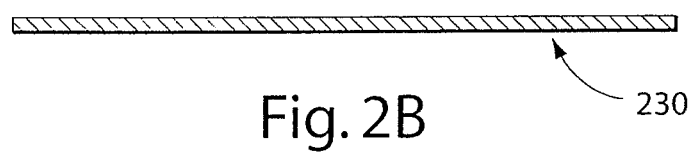
Figure 2C:
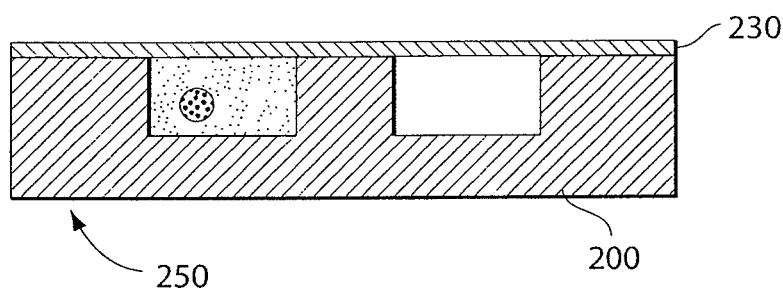
Figure 2D:
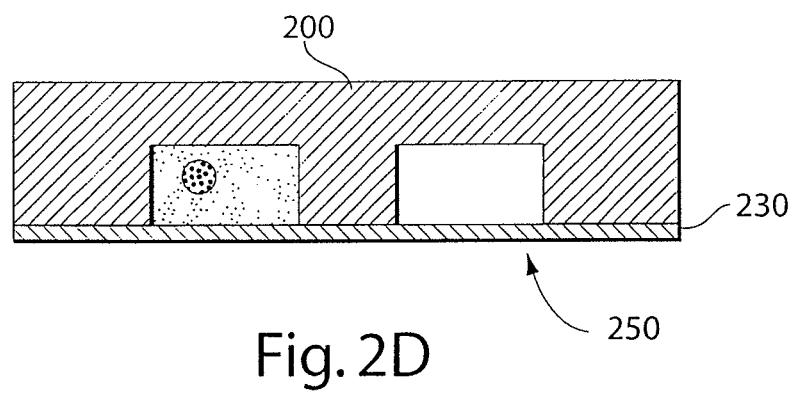

For example and referring to FIGS. 2A-2D, a moldable slab 200 may include a material, such as a cell 210 in a fluid medium 220. A substrate 230 (FIG. 2B) may be disposed on the moldable slab 200 to form test apparatus 250 (FIG. 2C). The test apparatus 250 is substantially fluid tight such that the test apparatus 250 may be oriented in any direction without substantial loss of fluid. For example, the test apparatus may be flipped over (FIG. 2D) to permit products secreted or produced by the cell 210 to settle, adsorb, become immobilized, etc. on a surface of the substrate 230 under gravitational force. While FIGS. 2A-2D) are shown with a cell 210 in the moldable slab 200, non-cellular species, such as proteins, catalysts, nanomaterials, etc. could instead be disposed in the moldable slab such that the proteins, catalysts, nanomaterials, etc. could be transferred to the substrate 230. Additional materials that may be used in the methods, apparatus and kits disclosed herein will be readily selected by the person of ordinary skill in the art, given the benefit of this disclosure. Illustrative materials that may be used to provide a substrate include, but are not limited to, glass, plastic (including both rigid and soft materials), polystyrene, polycarbonate, poly(dimethylsiloxane), nitrocellulose, poly(vinylidene fluoride) (PVDF), metals such as gold, palladium, platinum, silver and alloys thereof, steel, mixtures of any of these materials, and other materials that may be used to provide a moldable slab.

The substrate may be coated with a composition or compound that acts to retain material transferred from the moldable slab. In some examples, an entire surface of the substrate may be coated such that material may be retained on the entire surface. In other examples, select areas of a surface may include a composition or compound that acts to retain material transferred from the moldable slab. Selective coating may assist in formation of a plurality of "spots" or "patterns" on the substrate that can be assayed. For example, a coating that acts to retain material may be disposed over a mask which has openings spaced a suitable distance from each other to provide an array.

As material is transferred from the moldable slab, the material may be retained by the array coating and can be subsequently screened against one or more species. In certain examples, the composition or compound may act to adsorb the material, e.g., by trapping some portion of the material in a matrix by physisorption of material on the substrate may occur. Such physisorption may be, for example, adsorption of antibodies directly onto the substrate, adsorption of proteins recognizing the constant region of the antibody's structure (Fe portion), e.g., Protein A or G, adsorption of secondary antibodies recognizing the constant region of the antibody's structure (Fe portion), e.g., Goat anti-Mouse, or combination of proteins and antibodies, e.g., Protein G and secondary antibodies. Overall, the region of microwells on the PDMS slab matched regions of the microarray and the specificity of the antibody produced by the individual cells in wells could be determined from the microarray. Materials suitable for retaining a desired material on a substrate will be readily selected by the person of ordinary skill in the art, given the benefit of this disclosure.

In other examples, the substrate may include a linking group which can react with a portion of the material to assist in retaining material on the substrate. In some examples, the surface of the substrate may be chemically modified. For example, the surface of the substrate may include silanes on glass. Modification of the surface with silanes containing free amine or carboxylic acid groups for linking secondary antibodies to surface by NHS-ester activation and subsequent amide linkages may be used, for example. Modification of surface with silanes containing a free nitrile group for electrostatic capture of primary or secondary antibodies (See Bioconj. Chem., 1999, vol 10 pp 346-353) may also be used. Thiols on a metal, such as gold, palladium, silver or platinum, may be used. For example, modification of the surface with thiols containing free amine or carboxylic acid groups for linking secondary antibodies to surface by NHS-ester activation and subsequent amide linkages may be used. Modification of a surface with thiols containing a free nitrile group for electrostatic capture of primary or secondary antibodies may be used. Covalent modification of exposed functional groups on a polymeric surface to cross-link secondary antibodies to surface may be performed. Additional methods and compositions for chemically modifying a surface of the substrate will be selected by the person of ordinary skill in the art, given the benefit of this disclosure.

The material in the moldable slab may be attached to the substrate using moieties or tags appended to secreted molecules. For example, covalent modification of secondary antibodies with a chemical moiety recognized by a second chemical moiety immobilized on the surface of the substrate may be used to immobilize the secondary antibodies to the substrate. In an illustrative example, biotinylated antibodies along with streptavidin immobilized on a surface of the substrate may be used. Peptide sequences or proteins may be appended to the secreted molecule and used to retain the secreted molecule on a surface of the substrate. Addition of appended moieties to the secreted molecules is performed in a manner to avoid or minimize disruption of the native structure of the molecule to provide a secreted molecule that has a structure as close as possible to the native structure of the molecule. Moieties or tags are selected for appending to secreted molecules or other molecules disposed in a moldable slab.

Material is transferred from the moldable slab to the substrate such that a suitable amount is present to detect association. An effective amount of material will vary for different materials disposed on the substrate depending, for example, on binding constants, temperature, ionic strength, concentration, pattern size, etc. In some examples, an effective amount provides at least a detectable signal after a labeled species associates with the material disposed on the substrate. A detectable signal may vary depending on the technique or method used to detect association. For example, more material may be disposed on the substrate where calorimetric methods are used for detection, while less material may be disposed on the substrate where mass spectroscopy is used for detection. In certain examples, a sufficient amount of material is disposed to provide a concentration of about 1 attomole/cm$^2$ to about 1 micromole/cm$^2$, more particularly about 1 femtomole/cm$^2$ to about 100 nanomoles/cm$^2$, e.g., about 10 femtomoles/cm$^2$ to about 10 nanomoles/cm$^2$.

In certain configurations which involve a cell or a few cells disposed in a microwell of the moldable slab, the total time required for performing an assay is less than about 24-48 hours, more particularly less than a day, e.g., less than about 12 hours. For example, because the volume of each microwell may be a few nanoliters or less, the time required for a cell to express and/or secrete a detectable amount of material may be only a few hours, e.g., less than about 8-12 hours. Expression and/or secretion of the material is typically the rate limiting step in performing assays involving monoclonal antibodies and other materials. In many instances, association of the species, even after time is allowed to reach an equilibrium state, proceeds rapidly when compared to the time required to express the material. The significant time savings provided by the methods, apparatus and kits disclosed herein provides for a substantial increase in throughput to screen large numbers of unknown species against a known species. It is a significant advantage that certain embodiments of the methods, apparatus and kits disclosed herein can reduce screening time from months to less than a day.

The moldable slab may be loaded with a selected material by placing the material in a fluid, such as water, a buffer, a solvent or the like, and adding a suitable amount of the dissolved or suspended material to the moldable slab. Some material disposed in the moldable slab will be retained in the wells or chambers of the moldable slab. Additional material may be suspended in fluid on top of the moldable slab, e.g., not in the wells of the moldable slab. Such additional material may optionally be wicked away or removed using, for example, micropipets, filter paper, drying agents, air streams and the like, such that only the chambers or wells of the moldable slab retain material, such as cells, catalysts, etc. This process assists in distinguishing which wells in the moldable slab secreted a molecule or compound disposed on the substrate that associated with a known species, and provides for rapid recovery and further analysis of such molecule or compound from the moldable slab.

The methods, apparatus and kits described herein may be used to provide a material on a substrate that can be tested for a desired binding specificity. The species which the material on the substrate may be exposed to can vary depending on the nature of the material disposed on the substrate. For example, where the material disposed on the substrate is a monoclonal antibody, the monoclonal antibody may be exposed to an antigen, or series or antigens, to determine whether or not the monoclonal antibody may associate with the antigen. Where the material disposed on the substrate is a catalyst, a reactant may be exposed to the catalyst to determine whether or not the catalyst may associate with the reactant. Where the material disposed on the substrate is an enzyme, a potential enzyme substrate, or a potential enzyme substrate analog, may be exposed to the substrate to determine whether or not the enzyme and the potential enzyme substrate, a potential enzyme substrate analog, can associate with the enzyme disposed on the substrate.

Where the material disposed on the substrate is a cellular product produced only in a bacterial cell after successful transformation, the cellular product may be disposed on the substrate and screened with a known substance that binds to the cellular product to distinguish between bacterial cells that have a transformation product, e.g., a plasmid, phasmid, etc., and those that do not. In some examples, a cell, or a cell in a moldable slab, may be exposed to an antigen and any resulting cytokine or cytokines, e.g., monokines, lymphokines, etc., can be disposed on a substrate and screened against a species to determine if a particular type of cytokine is produced in response to antigen exposure. It will be within the ability of the person of ordinary skill in the art, given the benefit of this disclosure, to select suitable species to test for association with a material disposed on a substrate.

Referring to FIGS. 3A and 3B where a single microwell or chamber 305 of a moldable slab 300 is shown, substrate 310 may be placed in fluid communication with the moldable slab 300 such that a substantially fluid tight seal is formed to retain cell 330 within test apparatus 305. Cell 330 secretes cellular products 342 and 344 which become adsorbed to the substrate 310. Subsequent to adsorption of the cellular products 342 and 344, one or more known species, such as species 352 and species 354, may be exposed to the cellular products 342 and 344 for a sufficient period to allow association between the species and the cellular products if such association may occur. In this simple illustration, species 352 associates with cellular product 342, while species 354 does not associate with either of cellular products 342 or 344. Prior to detection, an optional washing step may occur to remove any excess species that do not associate with the products disposed on the substrate 310. Species 352 may contain a label, such as a fluorescent label, colorimetric label, etc. such that detection of the product 342—species 352 complex may be performed. While the illustrative example shown in FIGS. 3A-3D is shown with reference to a cell, non-cellular species, such as catalysts, nanomaterials, etc. may also be identified using similar methods.

One particularly useful application for the methods, apparatus and kits disclosed herein is to provide an array of unknown monoclonal antibodies disposed on a substrate. The generation of monoclonal antibodies have significant utility as research tools and are also highly valuable as potential drug candidates. Efficient screening methods have limited the number of candidate antibodies produced for therapeutic purposes. The uses of the methods, apparatus and kits disclosed herein can be extended, however, to use the array of secreting cells to assay the response of cells on a solid substrate and include screening any secreted material of interest from any cell type.

Examples of secreted materials include, for example, cytokines, chemokines, and pathogens such as viruses.

Examples of cell types that could be used include all classes of lymphocytes (e.g., B cells, T cells) and other cells specializing in secretion (for example, liver or kidney cells). Known antigens may be added to the array to determine which monoclonal antibodies could bind to the antigen. The known antigen may be added to each member of the array or different antigens may be added to some members in the array. In a typical configuration, more than one type of monoclonal antibody may be present at each array member such that the monoclonal antibodies may be screened batchwise to determine if any of the monoclonal antibodies in any particular array member can associate with the antigen. Such batchwise screening provides for rapid testing of a plurality of monoclonal antibodies. If one or more monoclonal antibodies in any particular array member do bind to the antigen, the monoclonal antibodies can be singled out individually for further testing to determine which particular monoclonal antibody, or monoclonal antibodies, in the array member can bind to the antigen.

Figure 4A:
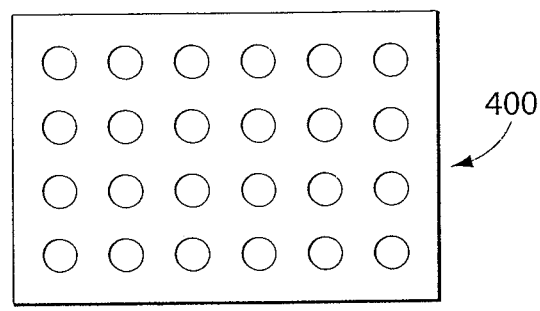
FIGS. 4A-4D are schematics of a membrane and its use with one or more substrates, in accordance with certain examples.
Figure 4B:
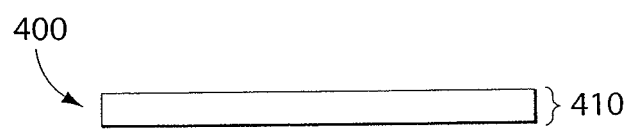
Figure 4C:
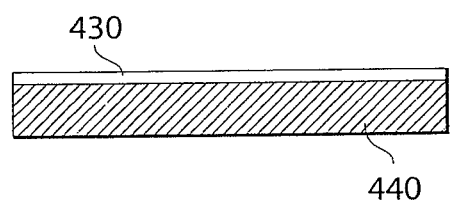
Figure 4D:
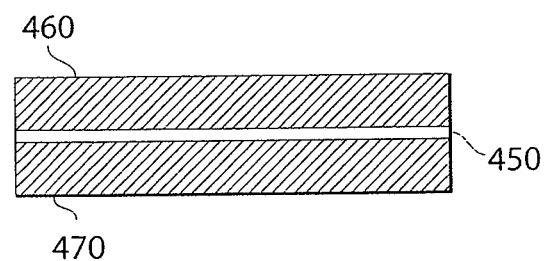

Instead of using a moldable slab in the Methods, apparatus and kits disclosed herein, alternative compositions may be used. For example, a membrane comprising a plurality of openings is placed on top of a substrate such as a glass or plastic slide, a metal plate, a porous filter material, or other rigid slab on which the membrane is in contact. In certain examples, the membrane may be disposed on the substrate and a substantially fluid tight seal may be formed between the membrane and the substrate. Referring to FIG. 4A, a membrane 400 is shown comprising a plurality of openings. In certain examples, the membrane may have a thickness 410 (FIG. 4B) of about 0.01 mm to about 1 mm, more particularly about 0.02 mm to about 0.2 mm, e.g., 0.03 mm to about 0.1 mm. In certain examples, the holes of the membrane may be sized and arranged to retain one or a few cells. In other examples, the holes may be sized and arranged such that each hole may retain a few nanoliters of fluid volume. This configuration would allow use in a manner similar to the wells of the moldable slab, but would have the advantage that two surfaces could be patterned or spotted simultaneously, or if the substrate surface was porous, the continuous exchange of nutrients through the back surface of the pattern transfer element may be permitted. Referring to FIG. 4C, a membrane 430 may be placed in contact with a substrate 440. Cells, such as hybridomas, bacterial cells, etc., may be disposed in the openings of the membrane 430, and products secreted by the cells may be adsorbed to the surface of substrate 440. Referring to FIG. 4D, a membrane 450 may be placed between a first substrate 460 and a second substrate 470. Cells within openings of membrane 450 may secrete products which can be disposed on a surface of substrate 460 and a surface of substrate 470. In embodiments where two or more substrates are simultaneously patterned using a membrane, it may be desirable to turn, invert or agitate the substrate-membrane-substrate assembly periodically to assist disposition of material on both substrate surfaces.

One or more of the substrates may include a compound or molecule that acts to retain secretion products on a surface of the substrate. One of the two substrates may also have a compound or molecule disposed on its surface that is capable of activating or modulating the secretion products of a cell or cells contained in the wells. Additional alternative configurations for disposing and/or transferring material to a substrate will be readily selected by the person of ordinary skill in the art, given the benefit of this disclosure. In some examples, each hole or opening of the membrane may be the same size and configuration as the other holes or openings in the membrane. In other examples, the holes or openings in the membrane may be sized differently such that differential disposition of material is patterned onto the substrate. In certain examples, the membrane may be produced using materials such as, for example, rubber, Teflon® polymer, polycarbonate, polydimethylsiloxane, and thermoset polymers. Additional materials, such as the moldable slab materials discussed herein, may also be used.

Identification of positive associations is performed using numerous suitable techniques including, for example, fluorescence, mass spectrometry, or other analytical methods used in traditional immunoassays (e.g., colorimetric methods). For example, the species added to the substrate may include a fluorescent label such that if the labeled species added to the substrate associates with the material disposed on the substrate, fluorescence emission may occur. Illustrative fluorescent labels include, for example, fluorescein isothiocyanate, didansyl chloride, lanthanides and lanthanide chelates, Alexafluor® dyes, inorganic semiconductor nanocrystals (e.g., quantum dots composed of II/VI or III/V semiconductors), and similar labels. Any fluorescence emissions may be detected visually or may be detected using suitable instruments, such as fluorescence microscopes, fluorimeters, cameras, or instruments that include a charge coupled device, a photomultiplier tube, a diode array and the like. Other labels that emit light, e.g., phosphorescent labels, chemiluminescent labels, etc., may also be used and detected using similar techniques as those used in connection with fluorescence detection.

The detectable moiety added to the substrate may include a colorimetric label such that if the labeled species added to the substrate associates with the material disposed on the substrate, and after addition of a suitable enzyme substrate, a color may result. For example, a colorimetric label is an enzyme, such as horseradish peroxidase. After an enzyme substrate, such as, for example, o-phenylenediamine dihydrochloride, is added to the enzyme a colored product is produced if the colorimetric label is present. The colored product may be detected visually or may be detected using suitable instruments such as, for example, UV/Visible instruments, plate readers, etc. In some examples, the colorimetric label may be a dye, e.g., an organic or an inorganic dye, such that if association occurs, the well or chamber remains colored, whereas if no association occurs, the well or chamber is clear and colorless. For example, if no association occurs the well appears clear or nearly colorless after unassociated labeled species are removed by washing.

Other detectable markers include a radiolabel. The radiolabel may be integrated into the species or may be added as a tag to the species. When a radiolabel is used, it may be desirable to construct the substrate with an absorbing material between array members to prevent or reduce crosstalk between the various members disposed on the substrate. Illustrative radiolabels include, but are not limited to, $^3$H, $^{14}$C, $^{32}$P, $^{33}$P, $^{35}$S and $^{125}$I. The species disposed on the substrate may be radiolabeled, and upon association, any radioactive emission from the species may be quenched by a molecule or group which associates with the species disposed on the substrate. Suitable radiolabels for use in the methods, apparatus and kits disclosed herein will be readily selected by the person of ordinary skill in the art, given the benefit of this disclosure.

Binding may be measured using mass spectroscopy. For example, the species may be allowed a sufficient time to associate and the contents (after optional washing steps) of a particular array member, or a selected array on a substrate, may be removed and analyzed using mass spectroscopy.

Numerous different mass spectroscopic techniques may be used. For example, matrix-assisted laser desorbed ionization (MALDI), electrospray ionization (ESI), fast atom bombardment (FAB), time of flight (TOF), MALDI/TOF, ESI/TOF, chemical ionization (CI), liquid secondary ion mass spectroscopy (LSIMS) or other mass spectroscopic techniques may be used. In some examples, tandem mass spectroscopy may be performed. Mass spectroscopic techniques are useful for distinguishing between association and non-association. In examples where mass spectroscopy is used, an array may be generated on an appropriate substrate (e.g., a metal plate for MALDI). The entire array may be probed with a mixture of proteins used for immunization (e.g., entire cell/lysates) and then characterized by mass spectrometry. Identification of proteins, lipids, or carbohydrates which are bound by specific antibodies may be accomplished, for example, by comparing the spectrometry data against databases of known biomolecules or compounds.

A proximity assay may also be used. For example, the species disposed on the substrate may be labeled with a radioactive label prior to transfer to the substrate. The species added to the transferred species on the substrate may include a fluorescent label, such that if association of the two species occurs, radioactive emission will excite the fluorescent label, and fluorescence emission may be detected as a positive indicator of association. Because this energy transfer process requires the radioactive label and the fluorescent label to be close, e.g., within a few microns, fluorescently labeled species that remain free in solution would not emit light. Such proximity methods have the added benefit that no washing steps or separation steps are required to determine if association occurs. Any fluorescence emission may be detected using the illustrative techniques disclosed herein, e.g., plate readers, flourimeters, etc. Suitable fluorescent and radioactive labels for performing proximity assays to assess association will be readily selected by the person of ordinary skill in the art, given the benefit of this disclosure.

A significant advantage of the methods, apparatus and kits disclosed herein that if association of the species does occur, then the material in the moldable slab, e.g., the cell or cells in a particular well or chamber, may be recovered and used for further analysis. In contrast, many existing methods do not permit recovery of cells for further use and/or analysis but instead require re-isolation and/or regrowth of the cells. For example, because the methods, apparatus and kits disclosed herein permit the cells to remain alive in the wells of the moldable slab, it is possible to produce multiple arrays for screening by stamping or patterning the array onto multiple substrates, and to retrieve positively identified cells for clonal expansion by micropipetting or similar techniques.

Figure 10:
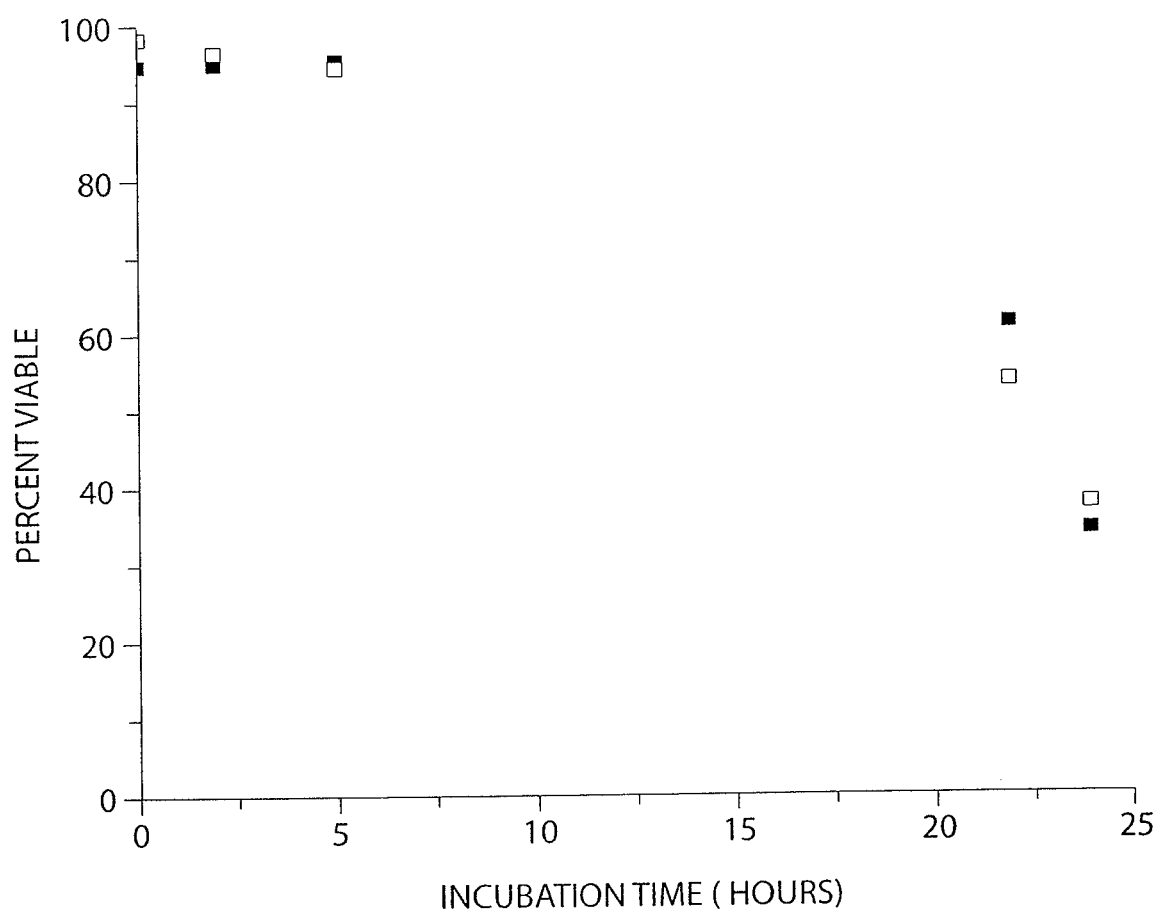
FIG. 10 is a graph showing the percent of viable cells as a function of incubation time, in accordance with certain examples.
Figure 11A:
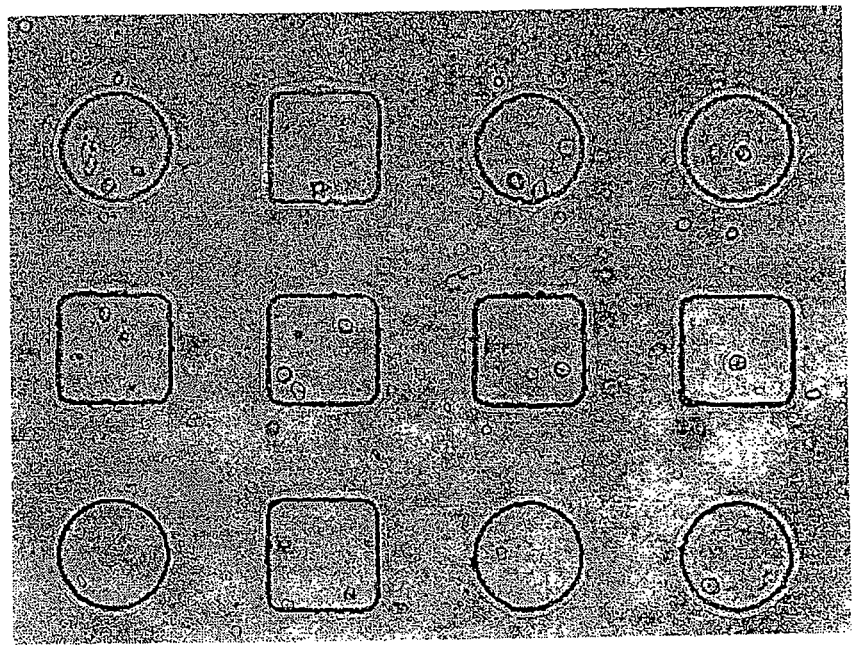
FIG. 11A, is a micrograph of Hyb9901 cells disposed in 100 micron diameter wells composed of polydimethylsiloxane
Figure 11B:
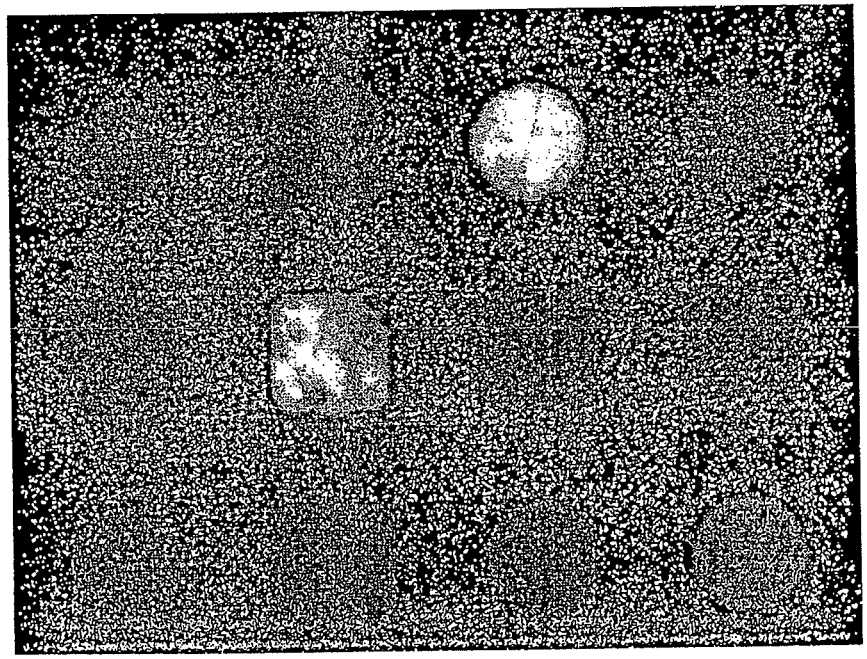
FIG. 11B is a micrograph of the slide, on which the array of microwells of FIG. 11A were disposed for 4 h, with physisorbed ovalbumin that associated with mouse anti-ovalbumin and was probed with a fluorescent secondary antibody (Goat-anti Mouse), in accordance with certain examples.
Figure 12A:
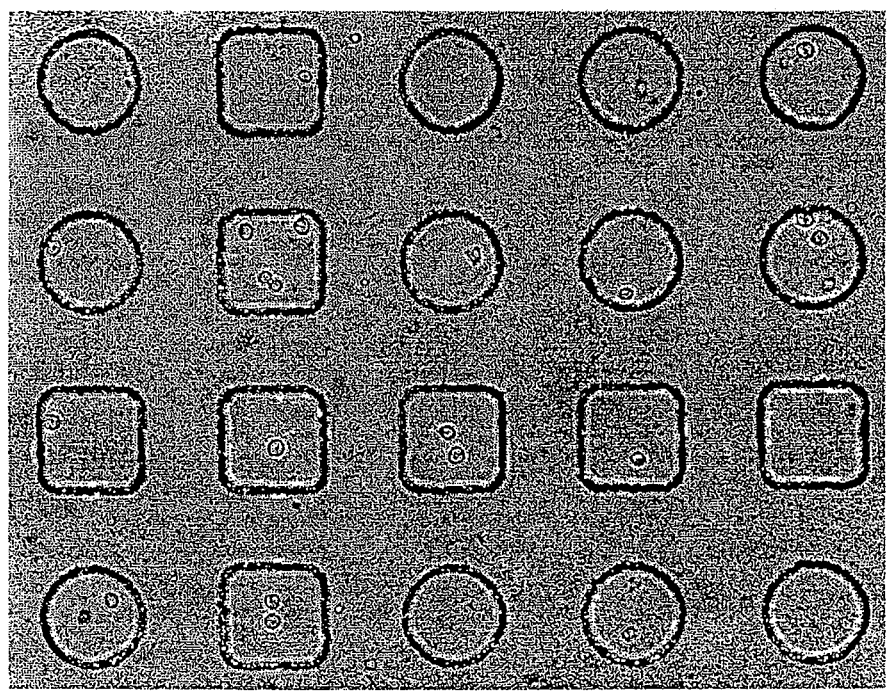
FIG. 12A is a micrograph of Hyb9901 cells disposed in 100 micron diameter wells composed of polydimethylsiloxane and FIG. 12B is a micrograph of physisorbed Protein G and secondary Ab (Goat-anti Mouse) on a glass slide, incubated with microwells of FIG. 12A for 4 hours (anti-ovalbumin hybridomas), after the glass slide was probed with fluorescent antigen (Ovalbumin-Alexa 488), in accordance with certain examples.
Figure 12B:
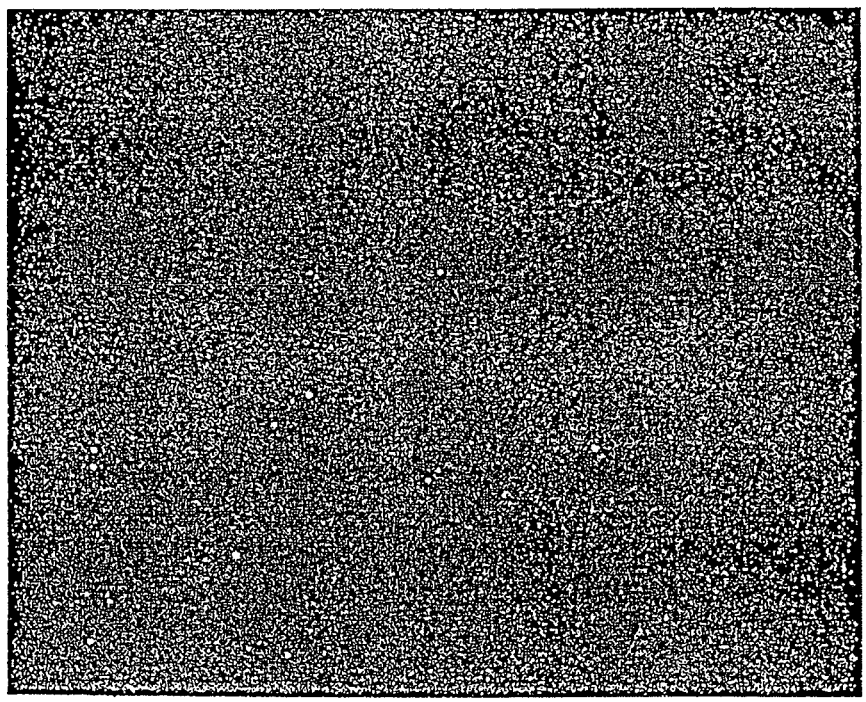

Cells confined in microwells and sealed against a glass slide (such that the total media available was limited to the volume of the microwell) may be maintained for about 5 hours and up to 24-48 hours, e.g., 1, 2, 6, 12, 18, 24, or 36 hours without a significant loss to viability. (FIG. 10). When a moldable slab is removed from a substrate and immersed in media, the cells remained loosely adhered to the bottom of the wells; vigorous rinsing or intentional extraction of the cells was required to dislodge them from the wells. Because the cells in the microwells remain viable after printing, the same set of microwells could produce multiple copies of an engraved microarray at different time points, by Elispot, FACS, ELISA, or other immunochemical methods is challenging. The resulting microarrays have a high degree of similarity, but are not identical; variations between specific spots may result from either fluctuation in the rate of secretion related to various stages of cell division or cell death.

The species (e.g., secreted cellular product), and/or cell producing the species, may be retrieved from the moldable slab using numerous techniques. For example, a micropipette may be used. An array of wells in the moldable slab can be coded or addressed to identify specific wells in the array to match positive hits from the substrate. Methods for coding the system include adjusting the spacing between wells, the shape of the wells, and the size of the wells. After removing the array of microwells from the substrate or the moldable slab, the wells can be immersed in appropriate cell culture media to maintain the viability of the cells until testing and/or characterization is complete. Extraction of the desired cell(s) from the identified wells can be performed with a micropipette. The extracted cell(s) may be expanded to generate a stable cell line, e.g., a stable hybridoma cell line. Expansion may be carried out in a microtiter plate (e.g., 96 or 384-well plate) containing suitable media to sustain cell viability. For example, in the case of a hybridoma cell line, a population of adherent feeder cells (e.g., fibroblasts) may be present to condition the media and provide a surface for cell-cell contact. Culturing the cells in the microwells for 1-3 days prior to extraction by micropipette would allow a few cycles of cell division within the microwells and make it possible to extract a few copies of the desired cell rather than a single copy. The exact conditions required to sustain the cells will vary depending on the cell type, and it will be within the ability of the person of ordinary skill in the art, given the benefit of this disclosure, to select suitable media and growth conditions to promote cell viability.

Microengraving offers three primary advantages over traditional screening by serial dilution and ELISA. First, microengraving allows the identification and segregation of the cells that secrete antigen-specific antibodies from a polyclonal mixture early in the screening process. The ability to isolate those cells should preserve slow-growing clones and rare clones (e.g., those that recognize particular epitopes of interest); traditional screening by serial dilution tends to favor fast-growing clones because the time required to attain detectable levels of antibodies is sufficiently long to allow outgrowth of the population tested. Second, segregation of cells early in the screening process reduces the labor and time required to maintain many individual clones while characterizing the antibodies produced for appropriate reactivity in immunochemical assays. Table 1, below, summarizes the significant differences in materials and time required for cloning by microengraving and serial dilution. Table 2, below, summarizes the cost analysis for microengraving and limited serial dilution. Third, microengraving simplifies the requirements for screening polyclonal populations to identify clones with different specificities. A single microarray can be screened with multiple, differentially labelled antigens, or fragments of antigens; equivalent screens by ELISA would require independent assays for each condition tested. The ability to immunize mice with mixtures of antigens furthers improve the rate of selection. A current disadvantage of microengraving is the manual retrieval of cells from the microwells. Existing or modified instruments for picking mammalian cells from colonies are useful for automated retrieval of cells, thereby further reducing the time involved in the screening process.

TABLE 1

Comparison of Time and Resources Required to Clone Hybridomas

| | Limiting Serial Dilution | Microengraving Method |
|---|---|---|
| Time after fusion until first screen | 7-13 days | 7-10 days |
| Number of wells (per plate) | 96-384 wells | 25,000-100,000 wells |
| Percent wells filled (average) | 33-100% (1-2 cells/well) | 50-80% (1-3 cells/well) |
| Number of cells (per plate) | ~32-384 cells | ~12,500-80,000 cells |
| Typical number of plates per screen | 10-100 | 1-10 |
| Total volume of fluid per well | 75-200 μL | 0.1-1 nL |
| Time till detectable levels of antibody are produced | 2-7 days | 2-4 h |
| Antigen required per screen (per plate) | 24-48 μg | ~0.75 μg |
| Use different antigens in a single screen? | No | Yes, multiple labels |
| Time per screen (culture + assay) | 7-10 days | ~10 h |
| Minimum screens to determine monoclonality | 2-3 rounds | 1-2 rounds |
| Minimum time for screening | 19-30 days | 1-2 days |
| Time required to maintain cultures between screens (per plate) | 5 min (every 2 days) | 5 min |
| Expected yield of desired hybridomas (per plate) | 0-1 | 0->>1 |

TABLE 2

Cost Analysis for Microengraving

| | Limiting Serial Dilution | Microengraving Method |
|---|---|---|
| Cost for Immunization of Mouse (1 antigen requires ~1 mg total material) | $120 (6 wks) | $120 (6 wks) |
| Time after fusion until first screen | 7-13 days | 7-10 days |
| *Cost of screening/plate†* | | |
| Labor (sorting and screening) | 1 hr FTE | 1 hr FTE |
| Actual Time (culture + assay) | 5-7 days | ~10 h |
| Supplies (plates and tips) | $8 | $12* |
| Reagents (antibodies & proteins) | $6.50 + 24-48 mg Ag | $0.50 + 1-7 mg Ag |
| Media | $12 | $6 |
| Total cost per plate ($) | $26.50 | $18.50 |
| Number of wells (per plate) | 96-384 wells | 25,000-100,000 wells |
| Percent wells filled (average) | 33-100% (1-2 cells/well) | 50-80% (1-3 cells/well) |
| Number of cells (per plate) | ~32-384 cells | ~12,500-80,000 cells |
| Cost per cell screened | $0.07-$0.83 | $0.0002-$0.001 |
| Minimum screens to determine monoclonality | 2-3 rounds | 1-2 rounds |
| Typical number of plates per screen | 10-100 | 1-10 |
| Total cost for cloning ONE hybridoma | $530-$7,950 | $18.50-$370 |
| Minimum time for screening | 19-30 days | 1-10 days |
| *(Cost should scale as~1/n with increasing numbers of recovered clones per screen)* | | |
| Expected yield of desired hybridomas (per plate) | 0-1 | 0->>1 |
| Maximum yield of unique monoclonal hybridomas (per plate) | 1 | ??? (>1) |
| Test different antigens in a single screen? | No | Yes, multiple labels (2-16) |

Microengraving enables similar assays for detecting a variety of secretions from large numbers of individual cells in a (semi)quantitative manner. The captured secretions represent the amounts produced over a fixed period of time, and analysis does not require monitoring a short-lived event such as calcium flux. The method is not limited to screening hybridomas derived from mouse splenocytes, but also can be applied to Epstein-Barr virus-transformed human B cells, and in principle, primary cells from peripheral blood or tissue. The methods are useful in measuring other secreted products, such as cytokines, for monitoring an immunological response and for measuring the frequency of cells within a population that produce a specific secreted factor in diagnostic assays. Multiplexed labeling, and the ability to generate multiple engravings from the same array of microwells, thereby allowing testing for the presence of multiple secreted products from single cells.

A protein or antigen is immobilized on a substrate, and then a species secreted by a cell is added to determine whether or not such species associates with the protein or antigen that is immobilized on the substrate. A labeled secondary antibody may then be added to probe for positive capture of the species. The protein or antigen is disposed on the substrate by transferal from a moldable slab or by disposal using conventional techniques such as, for example, pipetting. The labeled secondary antibody may be labeled with any of the illustrative labels disclosed herein, e.g., fluorescent labels, radioactive labels, colorimetric labels, etc. Detection may be accomplished using any of the methods disclosed herein, such as, for example, fluorescence, mass spectroscopy, etc., depending on the selected label.

The methods, apparatus and kits disclosed herein may be used to immobilize antibodies on monolayers of cells. For example, secretion of antibodies from wells of a moldable slab onto monolayers of fixed and permeabilized cells followed by treatment with a fluorescently labeled secondary antibody can provide a method to characterize antibodies by structural labeling within the cell. Optical microscopy would allow identification of antibodies labeling specific organelles. For example, organelles such as cytoskeleton, endoplasmic reticulum, Golgi apparatus or other organelles may be labeled.

The species that can be identified using the methods, apparatus and kits disclosed herein may be further characterized using conventional techniques, such as immunoprecipitation, Western blots, or other biochemical analysis to identify the specific species. For example, the monoclonal antibodies may be sequenced. X-ray crystallography, NMR analysis and the like may also be performed to characterize the structure of the identified species. Additional suitable techniques for characterizing the species identified using the technology disclosed herein will be readily selected by the person of ordinary skill in the art, given the benefit of this disclosure.

Engineered organisms may be used with the methods, apparatus and kits disclosed herein. For example, a modified Ig locus may be introduced into an animal (e.g., a $D^h$-/- or $J^h$-/- mouse) that includes a genetic encoded chemical structure for attaching antibodies secreted to the solid slab. For example, a recombinant Ig molecule includes a sortase signal peptide sequence onto the end of the Ig locus. This addition would produce antibodies with the sortase signal peptide expressed on the Fc portion of the antibody. Incubation of the cells in a media containing recombinant sortase enzymes on top of a substrate containing immobilized peptidoglycans allows covalent attachment of the antibody to the peptidoglycans via transpeptidation. Another illustrative example would include addition of a fragment of a ubiquitin-specific protease that includes the active catalytic site onto the end of the Ig locus. This addition would produce antibodies with a known reactive oligopeptide sequence expressed on the Fc portion of the antibody. Incubation of cells producing these labeled antibodies on top of a substrate containing an immobilized electrophile (e.g., vinyl methyl ester) would allow covalent attachment of the antibody to the surface. Such modifications may also be performed in bacterial cells, viruses, insect cell lines and the like.

Certain specific examples are described below to illustrate further the novel and inventive subject matter disclosed herein. The following materials and methods were used to demonstrate the compositions and analytical techniques described herein.

Figure 16C:
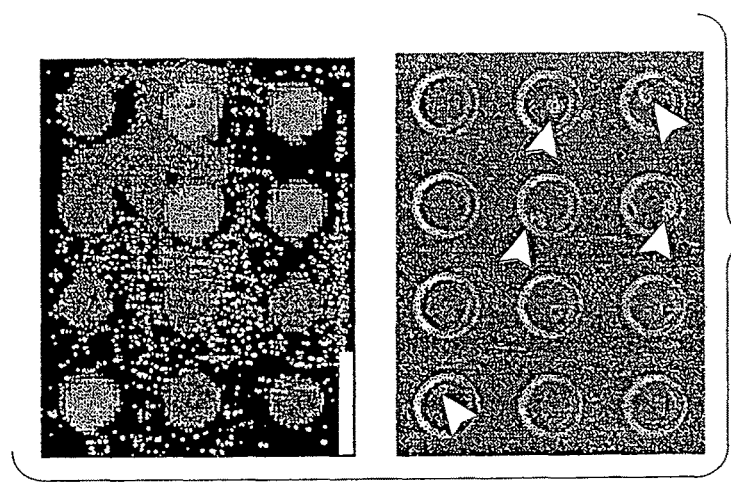
FIG. 16C is a fluorescence micrograph of a region of a microarray showing conjugation of captured antibody.
Figure 16A:
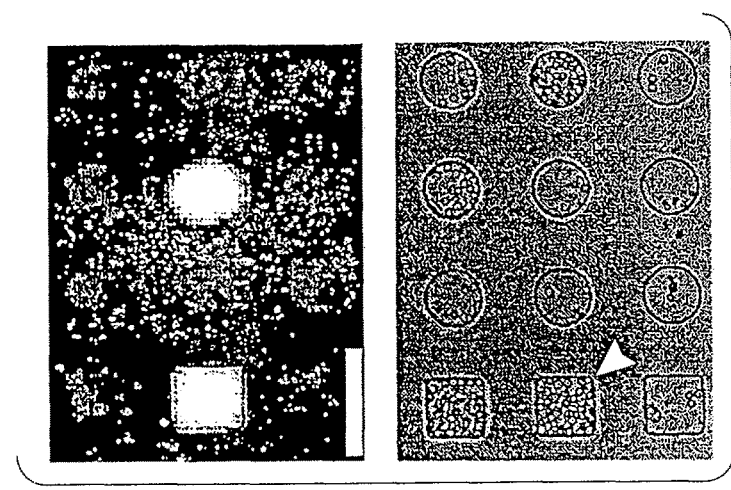
FIG. 16A is a fluorescence micrograph of a region of a microarray generated from a polyclonal mixture of cells and a phase contrast micrograph.
Figure 17A:
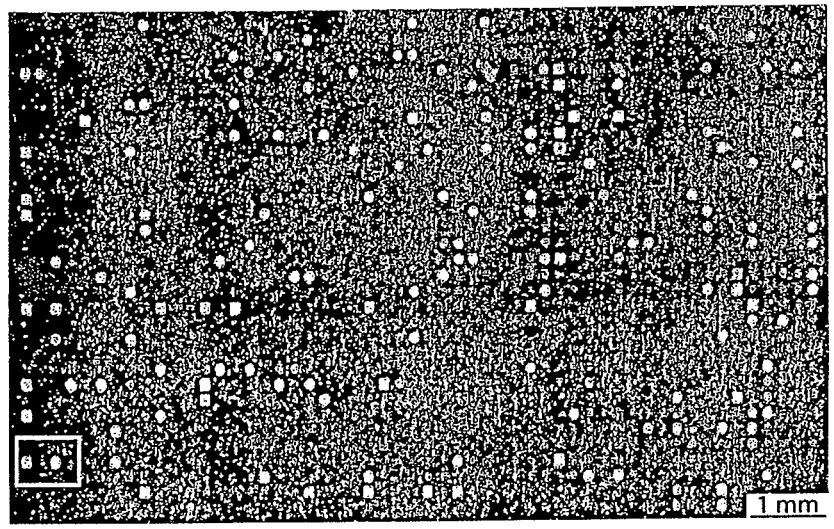
FIG. 17A is a micrograph showing spots generated from a polyclonal mixture of hybridomas that are reactive with fluorescently labeled H-2K$^b$ tetramers.
Figure 17B:
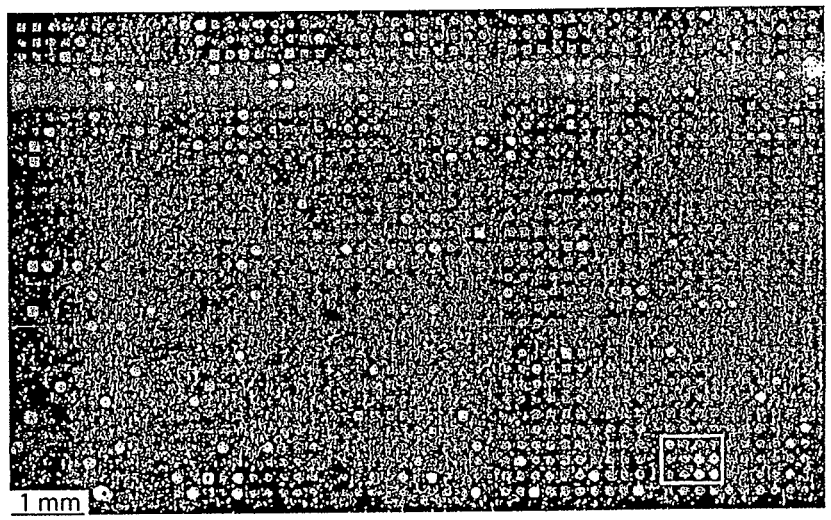
FIG. 17B is a micrograph showing spots generated from one expanded hybridoma (clone 136) that are reactive with fluorescently labeled H-2$^b$ tetramers (red) and goat-anti-mouse IgG (green).

The examples using known hybridomas suggested that it should be possible to identify rapidly cells producing antigen-specific antibodies within a polyclonal mixture and retrieve them for clonal expansion. Mice with peptide-loaded H-2$K^b$/streptavidin tetramers, and generated hybridomas by fusion of splenocytes with NS-1 cells were immunized according to standard protocols. Following bulk selection of the fused cells, polyclonal mixtures were loaded into arrays of microwells and incubated on glass slides coated with goat-anti-mouse IgG antibodies. The resulting microarrays were stained using tetramers of H-2$K^b$ prepared with fluorescently-labeled streptavidin (FIG. 16A and FIGS. 17A-B). Approximately 200,000 cells from the mixtures were screened across ten microarrays. 50 cells were arbitrarily selected to extract for expansion from the ~4,300 positive spots identified on the microarrays. The cells expanded in the microwells for four days (doubling every ~12-24 h) before being extracted using a micromanipulator and deposited into a 96-well plate, 42 clones survived extraction and subsequent expansion; of these clones, the supernatants of 17 of which showed strong responses by indirect ELISA relative to a control antibody (AF6-88.5).

Figure 16B:
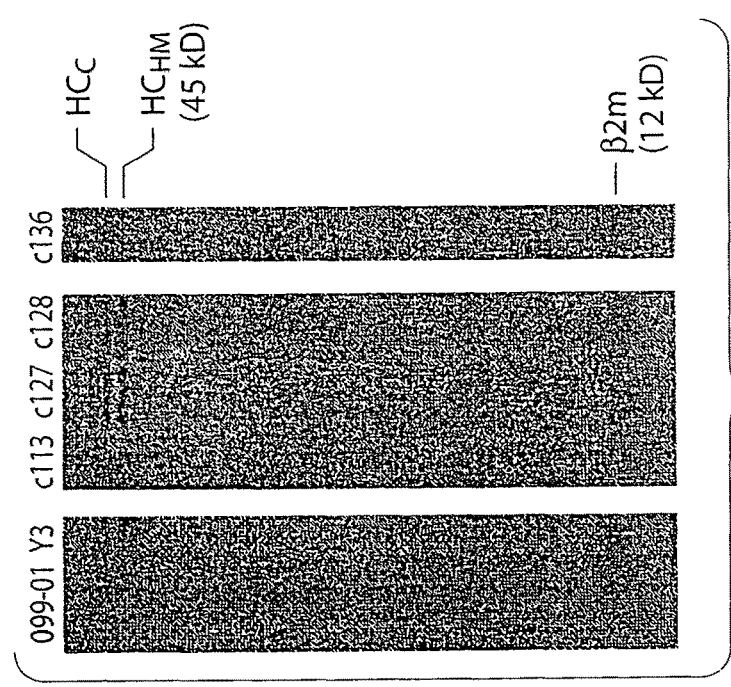
FIG. 16B is an autoradiograph of $^{35}$S-labelled H-2K$^b$ immunoprecipitated using supernatants from cultures containing Hyb 099-01, Y3, and four clones.

The specificity of the antibodies from four clones (c113, c127, c128, and c136) was tested further by the immunoprecipitation of properly assembled H-2$K^b$ molecules from detergent extracts prepared from $^{35}$S-methonine/cysteine-labeled EL4 cells (FIG. 16B). Three of the four clones recovered H-2$K^b$. No detectable amounts of IgG were present in the supernatants of the clone that did not recover H-2$K^b$ (c113), suggesting that this clone may represent a false positive selected from the combination of the microarray screen and indirect ELISA, or that it had lost its ability to produce the antibody of interest (chromosome loss or epigenetic change). The antibodies produced by clones 127, 128, and 136 were all IgG$_1$γ. SDS-PAGE of denatured $^{35}$S-labeled antibodies produced by clones 127 and 136 showed single bands that migrated differently for both the heavy and light chains; these data suggest that the hybridomas produce unique antibodies. To further evaluate clone 136, the cells were expanded, frozen, revived, and then used to prepare an engraved microarray (FIG. 16C and FIGS. 17A-B). Antibodies were captured on a slide coated with goat-anti-mouse IgG, and the array was probed with both fluorescent antigen (H-2$K^b$) and a fluorescent antibody (goat-anti-mouse IgG). This array showed that all cells in the population tested produced IgG that was also specific to H-2$K^b$.

Cell culture and purification methods are more specifically described herein. Cell types EL4, NS-1 (ATCC), HYB 099-01 (Statens Serum Institut, Copenhagen, Denmark) and Y3 cells were grown in Dulbecco's Modified Eagle Medium (DMEM) (Gibco, Grand Island, N.Y.) supplemented with 10% (v/v) fetal calf serum (FCS, Hyclone, Logan, Utah), 50 units penicillin/50 µg streptomycin, 20 mM HEPES, 50 µM 2-mercaptoethanol, 1 mM sodium pyruvate, and 0.1 mM nonessential amino acids (Gibco, Grand Island, N.Y.) at 37° C. (5% $CO_2$). The cells were split every 2 to 3 days under sterile conditions.

Peptides, having the sequences SIINFEKL (SEQ ID NO.: 1) and SIYRYYGL (SEQ ID NO.:2), were synthesized by standard Fmoc-based solid-phase peptide chemistry, confirmed by MALDI-MS and LC/MS analysis, and were used directly, without further purification. Murine β$_2$-microglobulin as well as a fusion protein of murine class I MHC heavy chain having a C-terminal biotinylation sequence were individually expressed, purified and reconstituted to H-2$K^b$ complexes. The recombinant proteins were expressed in *Escherichia coli* employing the isopropyl-β-D-thiogalactopyranoside (IPTG)-inducible pET vector system (Novagen) and BL21 (DE3) as an expression host. The recombinant proteins were isolated as inclusion bodies and dissolved under denaturing conditions (8 M of urea). Reconstitution was performed under dilute conditions in the presence of a large excess of the appropriate peptide. Subsequently, the monomeric, soluble H-2$K^b$-peptide complexes were appended with a biotin moiety under the agency of BirA biotin ligase (Avidity) and purified by size exclusion chromatography (Superdex 75, Amersham Biosciences) to remove aggregates and free biotin. For immunization, tetrameric complexes were produced through stepwise addition of the appropriate soluble MHC class I complex to Streptavidin (Invitrogen) to a final molar ratio of 4:1. For interrogation of the microarray, tetrameric complexes were formed in a similar manner using Streptavidin Alexa 546 (Invitrogen) or Streptavidin Alexa 647 (Invitrogen).

Balb/c female mice (8 weeks-old, Taconic) were immunized once every two weeks subcutaneously with an emulsified 1:1 mixture of antigen (25-35 µg dissolved in 100 µL PBS) and complete Freund's adjuvant (first immunization only) or incomplete Freund's adjuvant (Sigma-Aldrich, St. Louis, Mo.). Three days prior to tissue harvest, antigen (100 µg $H-2K^b$/tetramers in PBS) was injected intraperitoneally. The fusion of splenocytes with NS-1 cells was performed according to standard protocols. Media used for bulk selection were supplemented with 20% (v/v) FCS (Hyclone, Logan, Utah) and 10% (v/v) Hybridoma Cloning Factor (Bioveris, Gaithersburg, Md.), hypoxanthine aminopterin thymidine (HAT; ATCC, Manassas, Va.), hypoxanthine thymidine (HT; ATCC, Manassas, Va.), and 50% PEG (Sigma-Aldrich).

Example 1: Microengraving

Figure 5:
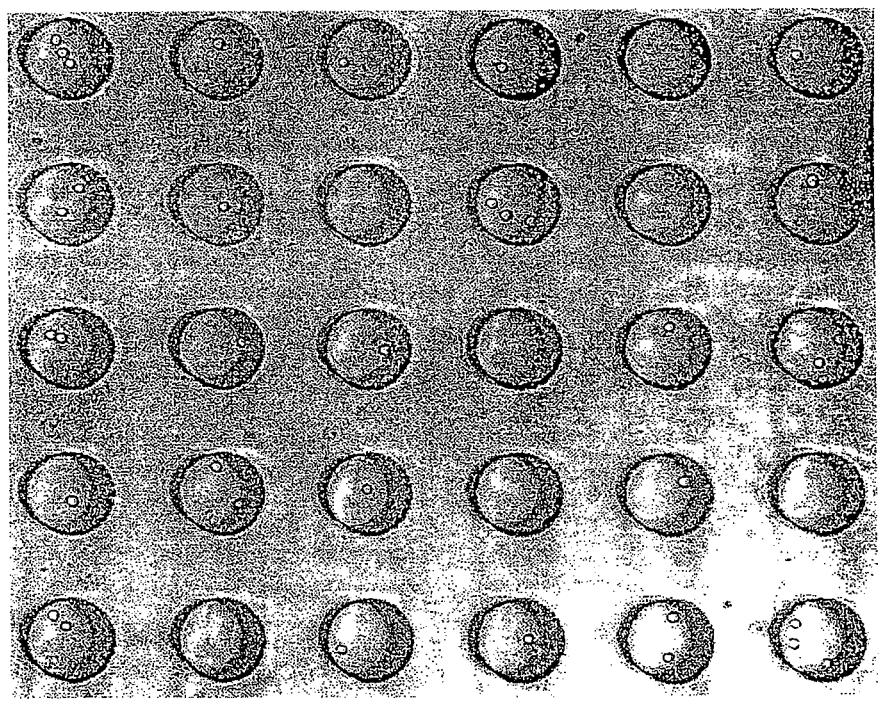
FIG. 5 is a photograph of Hyb9901 cells (anti-ovalbumin) disposed in 100 micron diameter microwells molded in poly(dimethylsiloxane), in accordance with certain examples.
Figure 7:
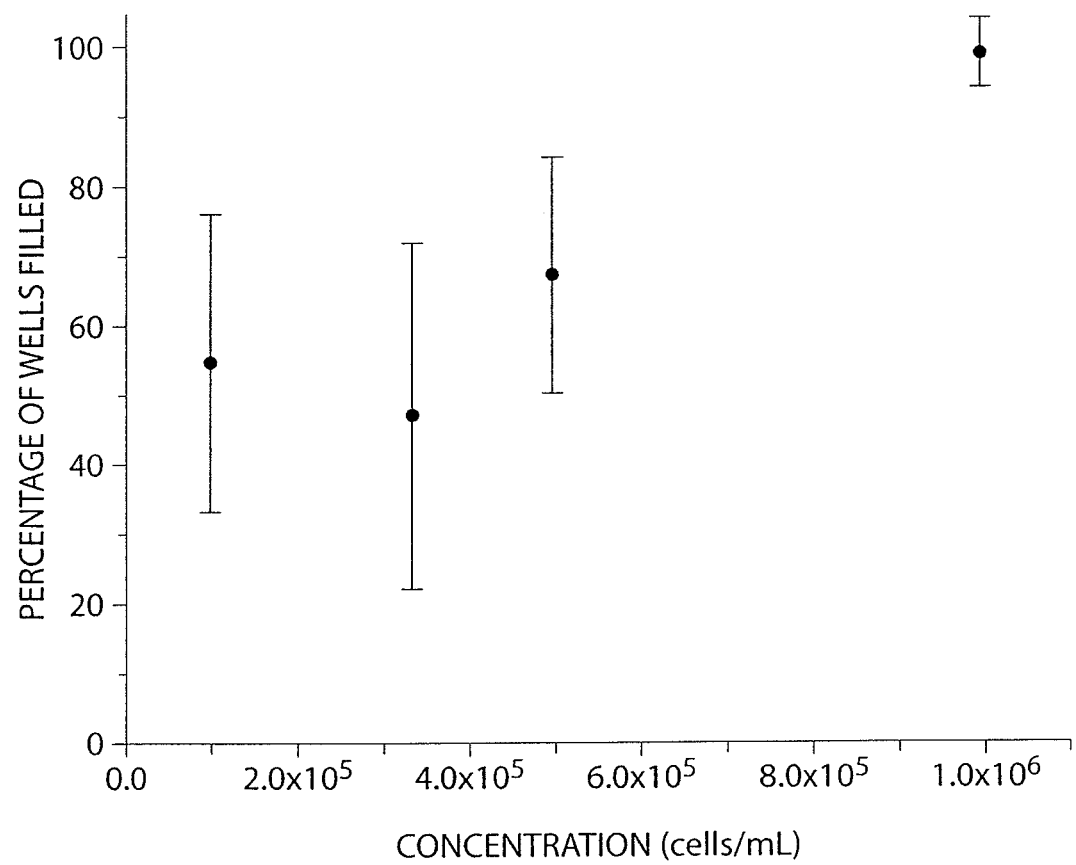
FIG. 7 is a graph showing the percentages of wells filled by one or more cells versus the concentration of cells, in accordance with certain examples.
Figure 8:
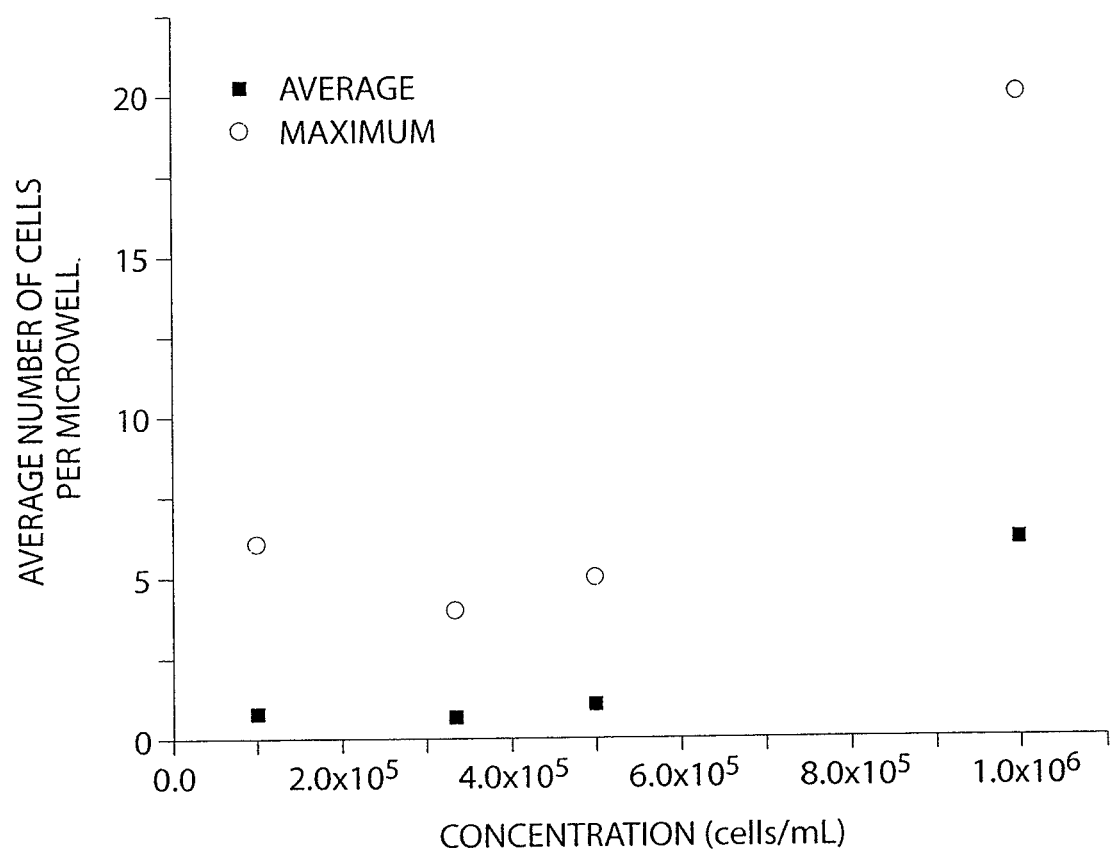
FIG. 8 is a graph showing the average number of cells per well versus the concentration of cells, in accordance with certain examples.
Figure 9:
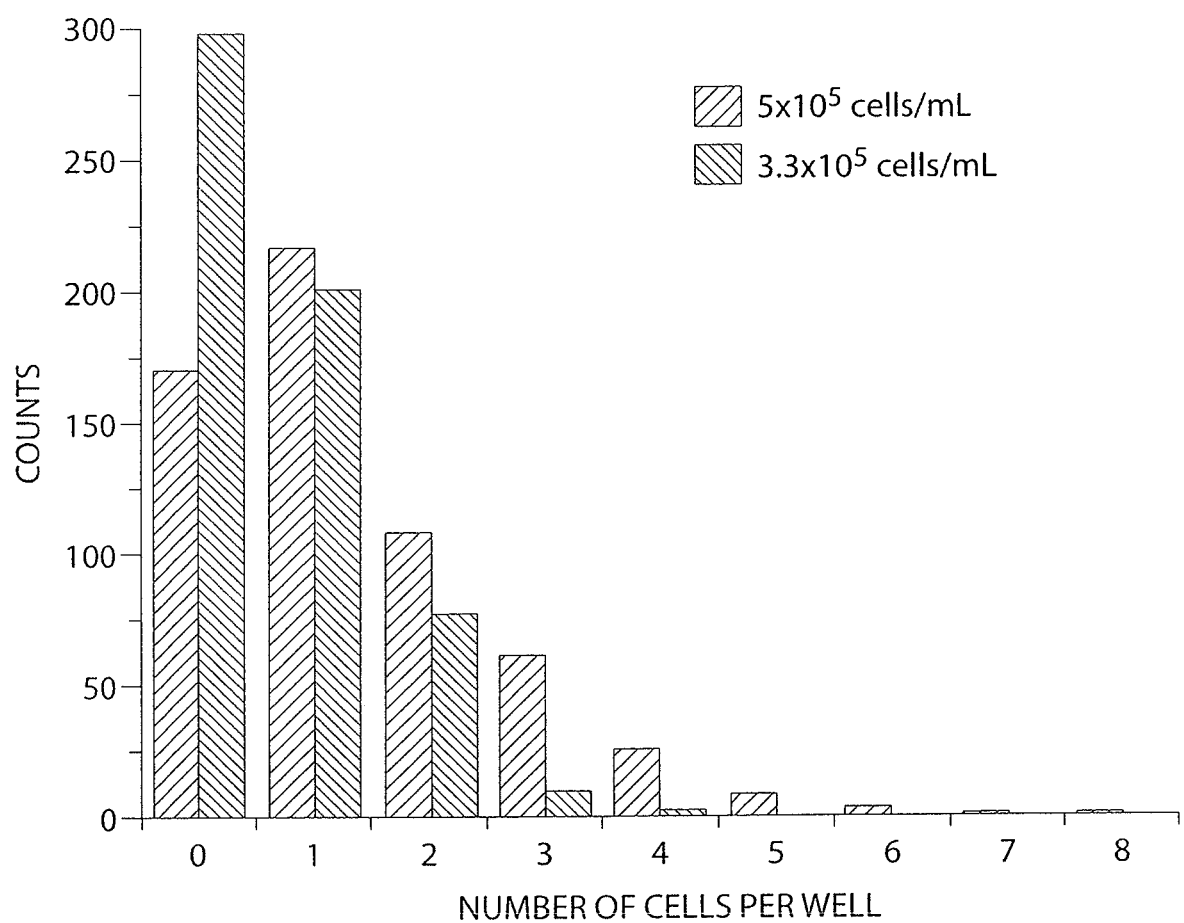
FIG. 9 is a bar graph showing the number of cells counted per well for two different concentrations of cells, in accordance with certain examples.

To prepare the microwells for engraving, cells were deposited on the surface of the PDMS slab at an appropriate dilution and allowed to settle before removing excess media, as shown in FIGS. 13A-B. The number of cells deposited per well depended on the concentration of cells, the volume applied, the time allowed for the cells to settle, the size of the microwells, and the size of the PDMS slab. (FIG. 6A). For slabs of PDMS ~25×50×5 $mm^3$ containing 25,000 wells (100 µm diameters separated by 100 µm), 0.5 mL of a cell suspension, ranging from $1×10^5$ to $5×10^5$ cells/mL, deposited for three to five minutes yielded one to three cells in ~50-75% of the wells (FIG. 5). The percentage of wells filled (FIG. 7) and the average number of cells per well (FIG. 8) were determined by counting the amount of cells in randomly determined fields with a lox lens and averaging the data collected from each microwell array. Referring to FIG. 7, as the concentration of cells present increased, the percentage of wells in the microarray filled by cells also increased. Referring to FIG. 8, as the concentration of cells present increased, the average number of cells per well also increased. Referring to FIG. 9, the results observed were consistent with using higher concentration of cells to increase the average number of cells in each well and using lower concentrations of cells to favor one or a few cells in each well. Cells confined in microwells and submerged in a large reservoir of culture media divided normally every 12-24 h for more than one week in culture.

Given the established rate of immunoglobulin (Ig) secretion for plasma cells and their derivatives (5,000 molecules/s), a single cell confined in a small volume (~0.1-1 nL) produced detectable concentrations of antibodies (~0.11 µM) in less than 5 h. Two established hybridomas—Hyb 099-01, anti-chicken ovalbumin, and Y3, anti-mouse $H-2K^b$ (major histocompatibility complex (MHC) class I)—were used to test the feasibility of the method for engraving microarrays of secreted antibodies on a glass slide. The antibodies secreted were detected in two ways (FIGS. 14A-E), In the first approach, secondary antibodies, goat anti-mouse Ig (gamma), were immobilized covalently on epoxide-functionalized slides; these slides were then incubated with an array of cells for 2 h, and interrogated with a mixture of fluorescently labeled antigens. Correlating the region of microwells on the PDMS slab with the matching region of the microarray data showed that (1) the fluorescent spots corresponded to the wells containing cells, (2) the level of non-specific binding of the fluorescently labeled proteins was low in regions where there were empty wells, and (3) the specificity of the antibody produced by the individual cells in wells could be determined from the microarray. (FIGS. 14A-C and FIGS. 12A-C).

Figure 14A:
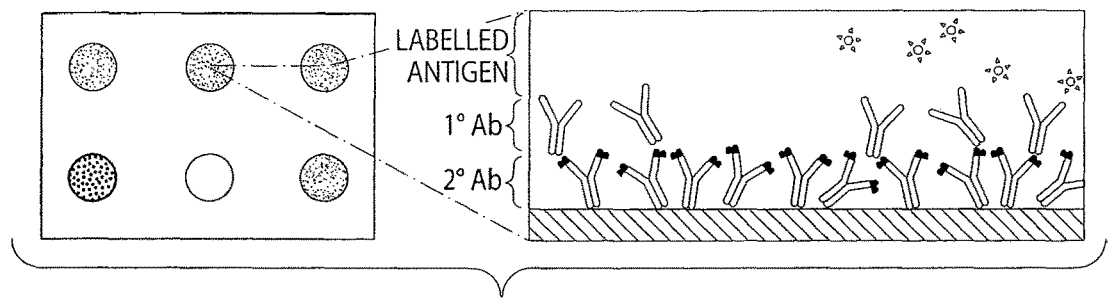
FIGS. 14A-E is a schematic displaying two methods for detection of antibodies on the surface of a substrate after microengraving.
Figure 14B:
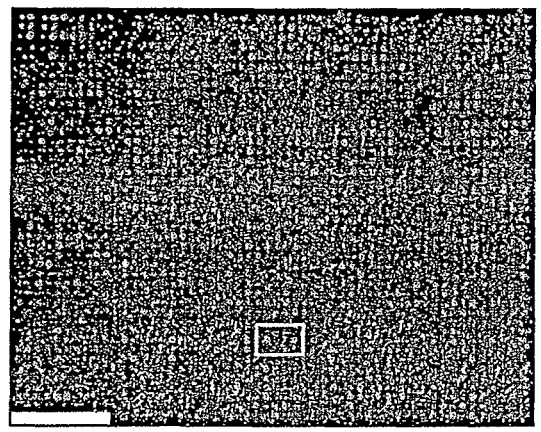
Figure 14C:
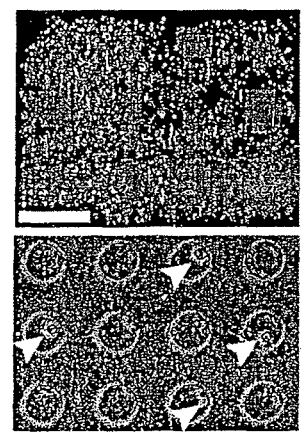
Figure 14D:
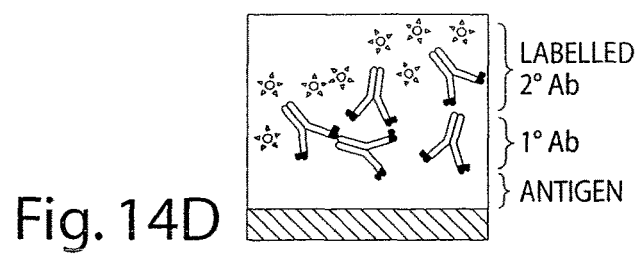
Figure 14E:
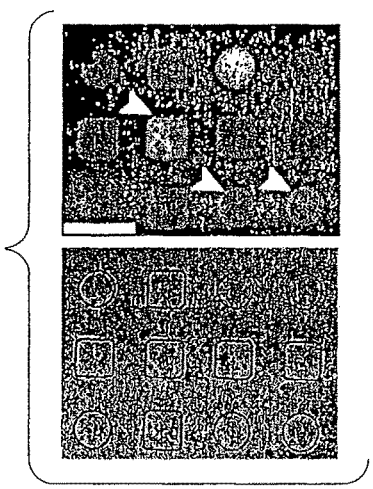

In a second approach similar to indirect ELISA, antigen—in this case, ovalbumin—was immobilized on slides by covalent attachment or by non-specific adsorption, the primary antibody was captured from cells contained in microwells, and the microarray was stained with a fluorescently labeled secondary antibody (goat anti-mouse IgG) (FIGS. 14D-E and FIGS. 11A-B). This format of the assay showed greater sensitivity to variations in the number of cells per well, and the amount of antibody secreted by individual cells, than the one using labeled antigens (FIG. 14A). The presence (or absence) of successful complexes formed between antibody and specific antigens was determined, and the relative rates of production by individual cells was assessed.

Cells confined in microwells and sealed against a glass slide (such that the total media available was limited to the volume of the microwell) showed little or no loss in viability for up to 5 h. (FIG. 10). When a PDMS slab was removed from a glass slide and immersed in media, the cells remained loosely adhered to the bottom of the wells; vigorous rinsing or intentional extraction of the cells was required to dislodge them from the wells.

Figure 15A:
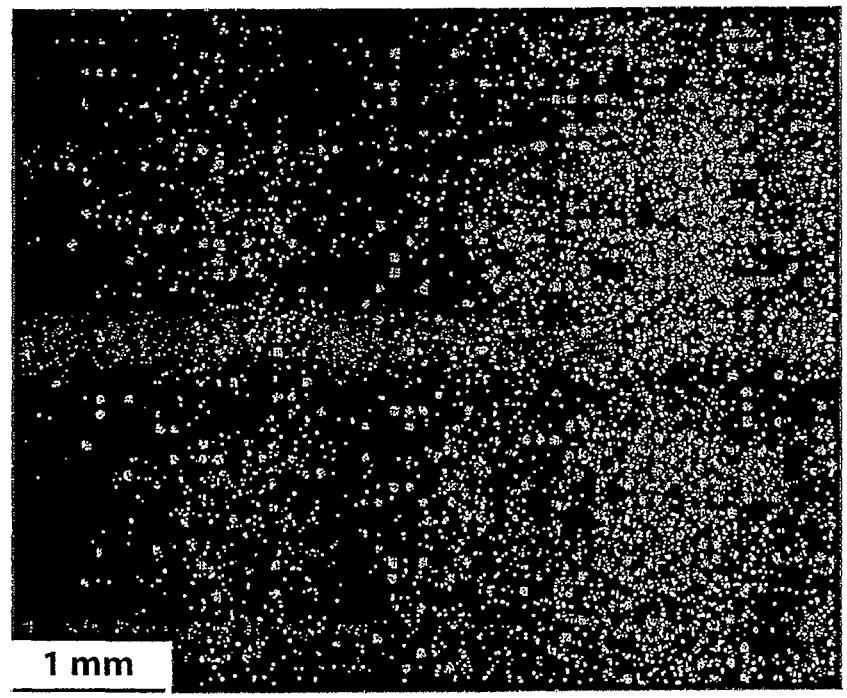
FIGS. 15A-B are fluorescence micrographs of two microarrays prepared sequentially using the same array of microwells.
Figure 15B:
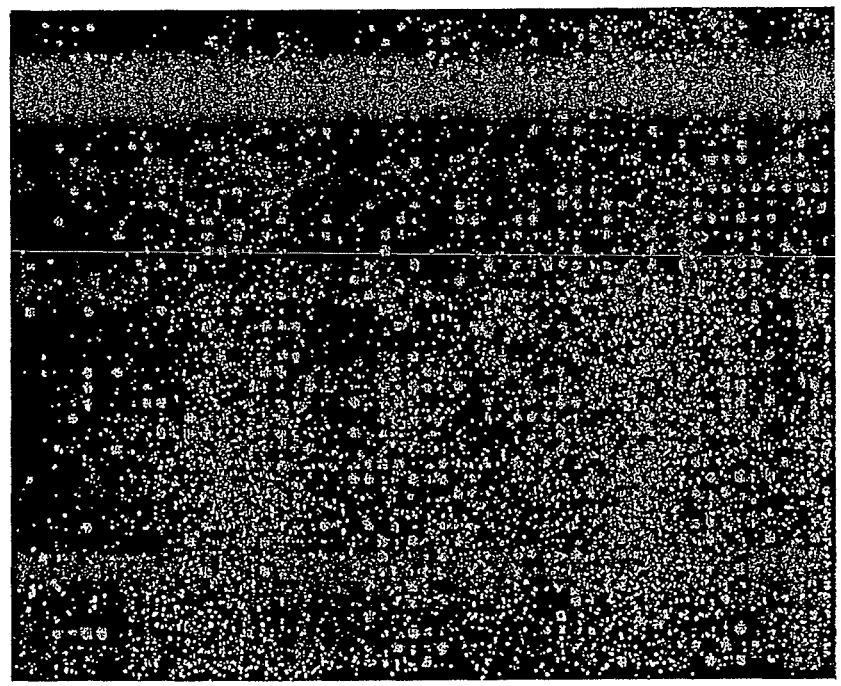

Determining the time-dependent variability of secretion from single cells by Elispot, FACS, ELISA, or other immunochemical methods is challenging. Because the cells in the microwells remain viable after printing, the same set of microwells were used to produce multiple copies of an engraved microarray at different time points. A set of microwells were incubated on a glass slide and was coated with secondary antibodies for 2 h. The microwells were removed and rinsed gently with fresh media, and the microwells were incubated on a second glass slide for another 2 h. (FIGS. 15A-B). The minimum incubation period is about 1 min to about 10 min, e.g., 30, 45 sec, 1, 2, 3, 5, 8 mm. Qualitative inspection of the resulting microarrays indicates that they have a high degree of similarity, but are not identical; variations between specific spots may result from either fluctuation in the rate of secretion related to various stages of cell division or cell death. The total number of replicas that can be made is about 100, more particularly about 4 to about 10 replicas using the same set of cells.

Microarray fabrication and methods for rapid high-throughput screening are described herein. The microwell arrays were fabricated in poly(dimethylsiloxane) (PDMS, Sylgard 184, Dow Corning) using photolithography and replica molding. One layer of photoresist (SU-8-100, Microchem, Newton, Mass.) was patterned on a 3 inch silicon wafer using a transparency photomask (CAD/Art Services, Bandon, Oreg.) to produce a master with a positive relief pattern of the microwell array. To facilitate removal of PDMS in subsequent steps, the masters were silanized by treatment with (tridecafluoro-1,1,2,2-tetrahydrooctyl)-1-trichlorosilane (UCT, Bristol, Pa.) in a vacuum desiccator for 1 h. PDMS was cast onto the master, cured for 2 h at 60° C., and peeled away. The PDMS was allowed to swell in hexanes for 24 h, deswell in acetone for 24 h, and then dry in an oven at 130° C. for 24 h to remove low-molecular weight oligomers. The microwell array was treated with an oxygen plasma (PDC-32G, Harrick, Ithaca, N.Y.) for 20 seconds; this process also sterilizes the array. The plasma-treated device was immersed in a solution of 10% w/v Bovine Serum Albumin (BSA) (0.01% sodium azide) for 1 h at room temperature and then rinsed with sterile phosphate buffered saline (PBS, Gibco, Grand Island, N.Y.). The estimated variation in height is less than 5%, the wells in the center of the array are taller than those on the outer edge of the array. The phase contrast images indicate the lateral dimensions vary less than 2%, the top of a single well is wider than the bottom of the same cell.

Glass slides (1"×3", VWR brand) were prepared and cleaned in "piranha" solution (conc. $H_2SO_4$: 30% $H_2O_2$, 7:3) at 70° C. for at least 1 hour. The slides were thoroughly rinsed with deionized water (Millipore, 18 MΩ) and immersed in an ethanolic solution containing 3-glycidoxy-propyltrimethoxysilane (95% ethanol, 1% v/v silane, pH adjusted to 4.5 using glacial acetic acid) at room temperature. The slides were removed after 1 hour, rinsed twice in 95% ethanol, and dried in an oven at 130° C. for 12 h. A solution of antigen (10-100 μg/mL ovalbumin (Sigma-Aldrich) or $K^b$-streptavidin tetramers,) or secondary antibody (200 μg/mL Goat anti-mouse Ig (gamma) Zymed, San Francisco, Calif.) in PBS was deposited on the surface of a slide under a coverslip (LifterSlip, Erie Scientific Company, Portsmouth, N.H.) and incubated overnight at 4° C. Following incubation, the slides were immersed in blocking buffer (PBS, 0.01% w/v $NaN_3$, 1% w/v BSA) for 1 h at 25° C. or stored overnight at 4° C. The slides were rinsed in PBS/Tween 20 (0.05% w/v, PBST), PBS, and then deionized water. They were spun dry for 5 min at 750 rpm immediately before being sealed against the microwell arrays.

A suspension of cells was then diluted to $1 \times 10^5$ cells/mL, in serum-containing media and 0.5-1 mL was pipetted onto the surface of the microwell array. The cells were allowed to settle for 3 minutes. The surface of the array was dewetted by applying a piece of extra thick filter paper (Bio-Rad, Hercules, Calif.) or by vacuum aspiration at one edge of the array while tilting the array. The percentage of wells filled and the average number of cells per well were determined by counting the number of cells in randomly-determined viewing fields with a 10× lens and averaging data collected from multiple microwell arrays.

To engrave the microarray, an array of microwells filled with cells and dewetted of excess media was placed well-side-down on the surface of a treated, dry glass slide. The combination of the array and glass slide was sandwiched together in a hybridization chamber (DT-1001, Die-Tech, San Jose, Calif.); the screws used to clamp the chamber together were tightened just until finger-tight. The entire assembly was incubated at 37° C. for 2-4 h. After incubation, the treated glass slide was removed from the surface of the microwell array and immediately immersed in blocking buffer (1% BSA/0.05% Tween 20/PBS), and agitated for 1 h at room temperature. After placing the glass slide in blocking buffer, the microwell array was quickly immersed in a bath of pre-warmed media before media contained in the microwells completely evaporated. (FIGS. 6A-E)

After blocking in preparation for interrogation of the microarray, glass slides were rinsed with PBST, PBS, and then deionized water for 5 min each; the slides were spun dry for 5 min at 750 rpm. A solution of either goat anti-mouse secondary antibody (Alexa Fluor 488 or 532, Invitrogen) or fluorescent antigen (e.g. 10 μg/mL Ovalbumin-Alexa Fluor 488 or 555 conjugate (Invitrogen) or $K^b$ tetramers prepared using streptavidin-Alexa 546 or 647 (Invitrogen) in PBS (80 μl)) was deposited on the surface of a slide under a coverslip (LifterSlip, Erie Scientific Company, Portsmouth, N.H.) and incubated in the dark for 1 h at room temperature. The slides were rinsed with PBST, PBS, and deionized water, and spun dry for 5 min at 750 rpm. The slides were imaged with a GenePix 4000B microarray scanner (Molecular Devices, Sunnyvale, Calif.) using 532 and 635 nm lasers and factory-installed emission filters. The lasers were used at 100% power and the PMT gain was set between 600 and 900 to maximize the dynamic range of the detector without saturation. Images of the microarrays were analyzed using GenePix Pro 6.1 (Molecular Devices, Sunnyvale, Calif.). Color ratio images were generated in GenePix and saved in the red and green channels of a 24-bit TIFF file. Background intensities were subtracted using median values measured in regions between individual spots of the array. The signal-to-noise ratio for a given positive spot in the array to negative (or background) spots within the same subarray was calculated by dividing the sum of the median intensity values from each channel for a given spot by the average sum of median intensity values for the negative spots determined from at least 20 negative spots. The mean values reported are the average of at least 128 positive spots from more than 12 subarrays.

In order to perform microscopy and micromanipulation, phase contrast images were acquired using Metamorph software (v6.3r3, Molecular Devices, Sunnyvale, Calif.) and an inverted microscope (Nikon Eclipse TE2000-E) equipped with a Hamamatsu ORCA AG camera. Cells were retrieved from individual wells using a micromanipulator (IM-9A, Narishige, Tokyo, Japan) fitted with hand-drawn capillaries (GC-1). To withdraw the contents of a well, the array of microwells was positioned on the microscope under a layer of media (~1 mL), and a capillary with an outer diameter of 100 μm (inner diameter ~50 μm) was positioned directly over the top of an appropriate well. A small volume (~1-5 μL) was withdrawn with the affixed syringe until the cells were removed from the well successfully. The tip was then transferred into a well of a 96-well plate containing 200 μL media (10% hybridoma cloning factor) and the cell(s) expelled into the volume. Both extraction from the microwell and deposition of the cells into another container (96-well plate) were monitored visually to ensure the transfer of the cells into and out of the tip.

Figure 18:
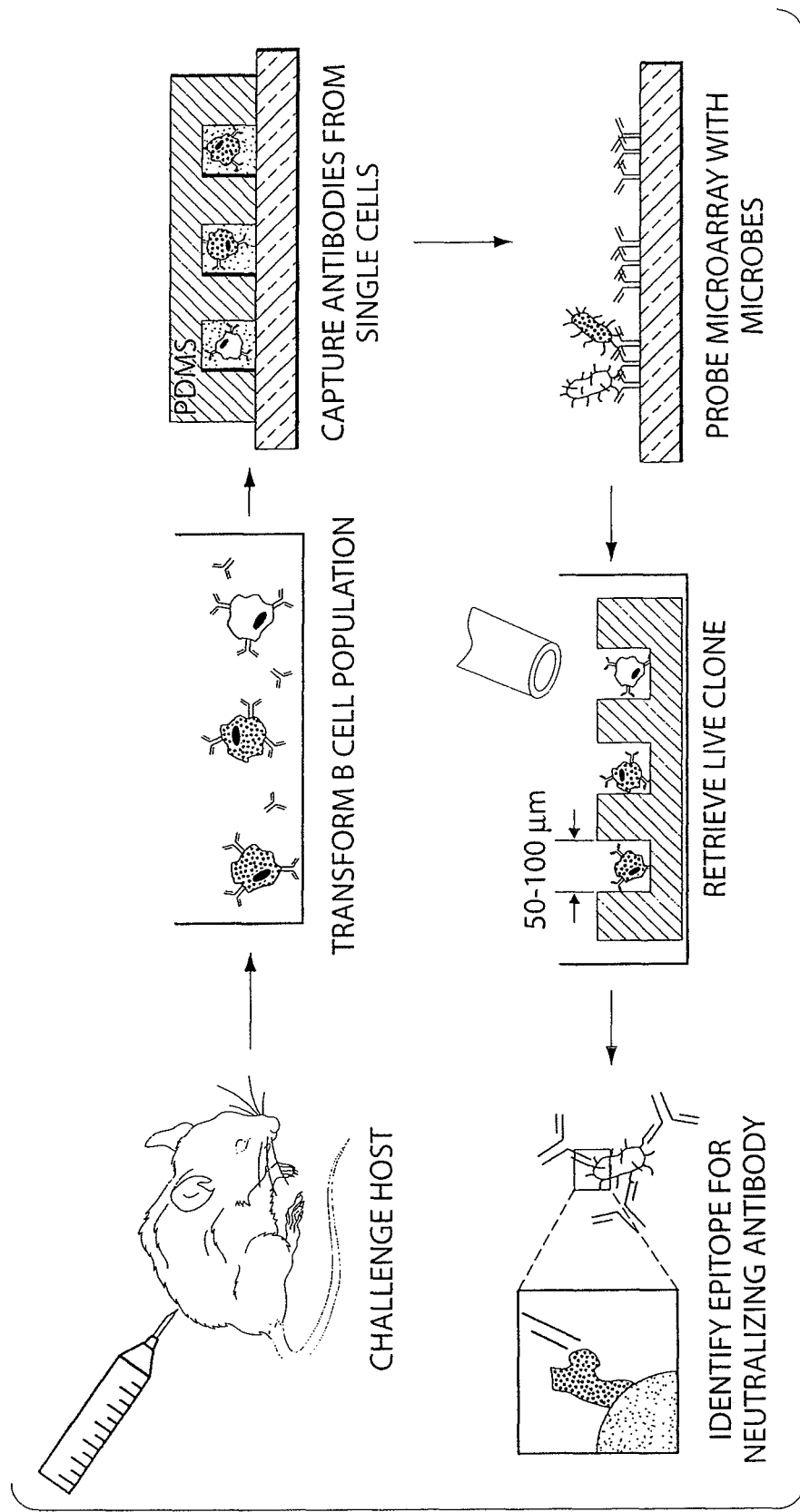
FIG. 18 is a drawing of a schematic illustration of proposed method for identifying antibodies that bind surface-expressed epitopes on a pathogen.

Example 2: Identification of Antibodies Specific for Surface Epitopes of Infectious Agents The methods described herein are useful to identify antibodies reactive against surface-exposed antigens present on infectious agents (bacteria, viruses, fungi), e.g., i) to identify new therapeutic agents for use in passive immunizations and ii) to discover candidate antigens for the development of new vaccines intended to invoke a protective humoral immune response. Memory B cells from convalescent human patients for other diseases, e.g., *Aspergillus* and malaria, are immortalized and their secreted products are screened using the engraved microarray. A schematic illustration (FIG. 18) of the method for identifying antibodies that bind surface-expressed epitopes on a pathogen. B cells are derived from an inoculated animal or a blood sample from a convalescent patient and screening with different serotypes or mutants of the pathogens should bias the screen for specific types of antibodies—for example, serotype-independent ones.

Microarrays of antibodies from a polyclonal mixture of cells are screened using whole pathogens; competitive assays using multiple serotypes or genetic variants allow systematic analysis of a range of pathogens (bacteria, fungi, viruses). Subsequent characterization of the antigens recognized by identified antibodies can provide a catalog of candidate antigens for developing a vaccine against the agent. The antibodies themselves are useful for passive immunization strategies. For example, target antigens are identified using a mouse model and a human pathogen, e.g., opportunistic fungal pathogen (*Cryptococcus neoformans*) that affects immunocompromised humans. Another strategy utilizes screening transformed populations of memory B cells from convalescent individuals. Translational research is used to assess value of identified antibodies or epitopes for passive immunization or development of vaccines.

Figure 19A:
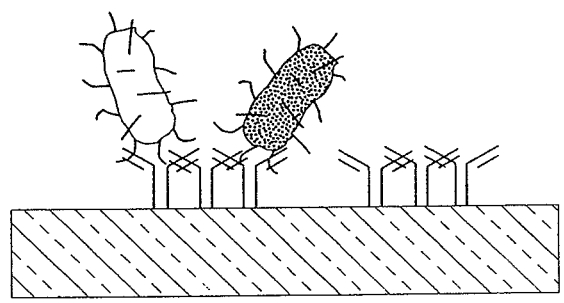
FIG. 19A is a graphic of the capture of different serotypes of the same microbe.

Using a mouse model for human disease, mice are immunized with fixed (or heat-inactivated) pathogens or inoculated with sub-lethal dosages by appropriate routes (e.g., inhalation, sub-cutaneous injection). Hybridomas are prepared from splenocytes by poly(ethylene-glycol)-mediated fusion with mouse myeloma cells (NS-1, Sp2/0). After bulk chemical selection of the surviving hybridomas, the growing polyclonal populations are loaded into microwells and used to engrave arrays of polyclonal antibodies (FIGS. 13A-D). A unique advantage that engraved microarrays afford over other methods for screening antibodies against antigens (enzyme-linked immununosorbant assays, flow cytometry) is the ability to design the probes for the array in a manner that biases the search for specific reactivity (FIG. 19A). On arrays generated using hybridomas prepared from mice challenged with *C. neoformans*, differentially-labeled variants of *C. neoformans* is used to identify two types of antibodies: 1) serotype-independent antibodies, and 2) antibodies recognizing antigens other than the glucuronoxylomannan layer (GXM) that masks much of the exposed surface on *C. neoformans*. For the first type, there are three serotypes of *C. neoformans* known to cause human disease (A, B, and C). Each variant is labeled with a different fluorophore (e.g., N-hydroxyl-succinimide Alexafluor 488, 532, or 647) and the array is incubated with a suspension of these yeast, which lead to some antibodies capable of binding all three serotypes.

Figure 19B:
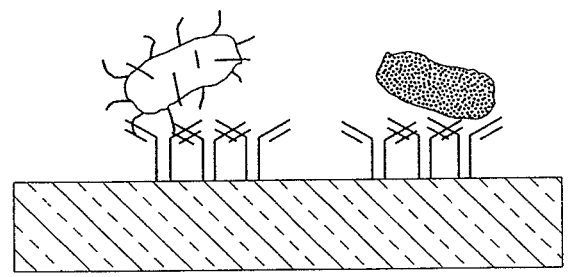
FIG. 19B is a drawing of the capture of altered microbe (genetic mutant, drug, enzyme-treated) to discover rare epitopes.

In a second approach, drug-treated wild type variants are used to identify antibodies recognizing epitopes on the surface other than GXM. Common anti-fungal agents, echinocandins, can disrupt the formation of the GXM layer, and allow access to the underlying cellular surface. (FIG. 19B), Such antibodies could supplement the use of drugs to treat an infection by improving the ability of the host's immune system to clear cells lacking mannan layers.

Antigen-specific clones are identified and retrieved by micromanipulation. The clonality and diversity of the antibodies produced are characterized by isotype, by SDS-PAGE gel electrophoresis of immunoprecipitated $^{35}$S-labeled antibodies, and by genetic sequencing. Also, in vitro assays are used to determine the extent to which individual monoclonal antibodies, or oligoclonal mixtures, confer protection via enhanced opsonization and phagocytosis of *C. neoformans* by macrophages or dendritic cells. A transgenic mouse that cannot produce circulating immunoglobulins (AID−/−, μS−/−) provides a background for measuring the usefulness of passive immunization in vivo without convolving a host-derived antibody response.

The disclosed method, apparatus and kits identifies epitopes recognized by neutralizing antibodies. The selected antibodies are those recovered antibodies that recognize a specific protein from the pathogen by immunoprecipitation or immunoblotting detergent-solubilized lysates of the bacteria, virus, or fungus. Specific staining with the monoclonal antibody and subsequent analysis by mass spectrometry allows identification of the protein recognized. Additional analysis using synthetic peptide libraries based on the sequence of the protein likely is used to refine the identity of a specific epitope, i.e., fine mapping.

In the event that an antibody binds the intact pathogen, but does not immunoprecipitate or stain a protein from a lysate, the identity of the antigen is deter mined as follows. First, for viruses and yeast, the whole microbe and corresponding lysates are treated with glycosidases, and subsequently, treated with the antibody to determine if binding is conserved after deglycosylation. This approach has led to successful recognition of carbohydrate epitopes essential for binding anti-HIV antibodies specific for gp120 (2G12 epitope). Second, tor bacteria, identification of non-proteinaceous epitopes would require disruption of pathways involved in surface-expression of glycolipids or other cell-wall components. For many bacterial pathogens (e.g., *Salmonella enteritidis*), a range of mutant strains exist that are used to deduce the component recognized by an antibody.

Figure 20:
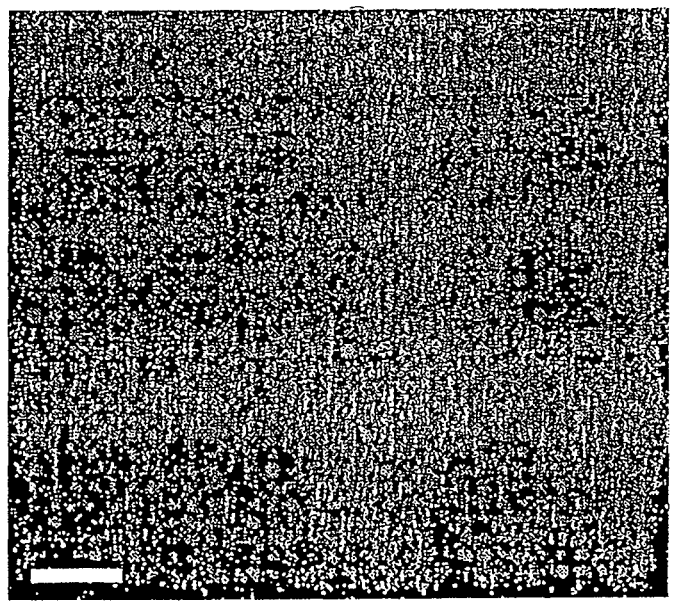
FIG. 20 is a fluorescence micrograph of human IgG captured by microengraving with EBV-transformed B cells and labeled with Alexa 488-goat-anti-human IgG.

Though mouse and humanized antibodies have had utility as therapeutic agents, it is increasingly understood that fully human antibodies induce fewer side effects than chimeric or transgenic ones. The method, described herein to identify and retrieve transformed human memory B cells producing human antibodies. Blood samples from convalescent individuals recovered from infectious diseases, e.g., *Aspergillus*, malaria, and influenza and transform the populations of human memory B cells in these samples by incubation with Epstein-Barr virus and a cocktail of suitable stimulants (CpG DNA, cytokines). Secreted human IgG by microengraving from such cells can be detected using the disclosed method, apparatus and kits (FIG. 20). These methods identify antibodies for use in passive immunizations, and identify what epitopes on a pathogen instigate a humoral immune response.

Figure 21:
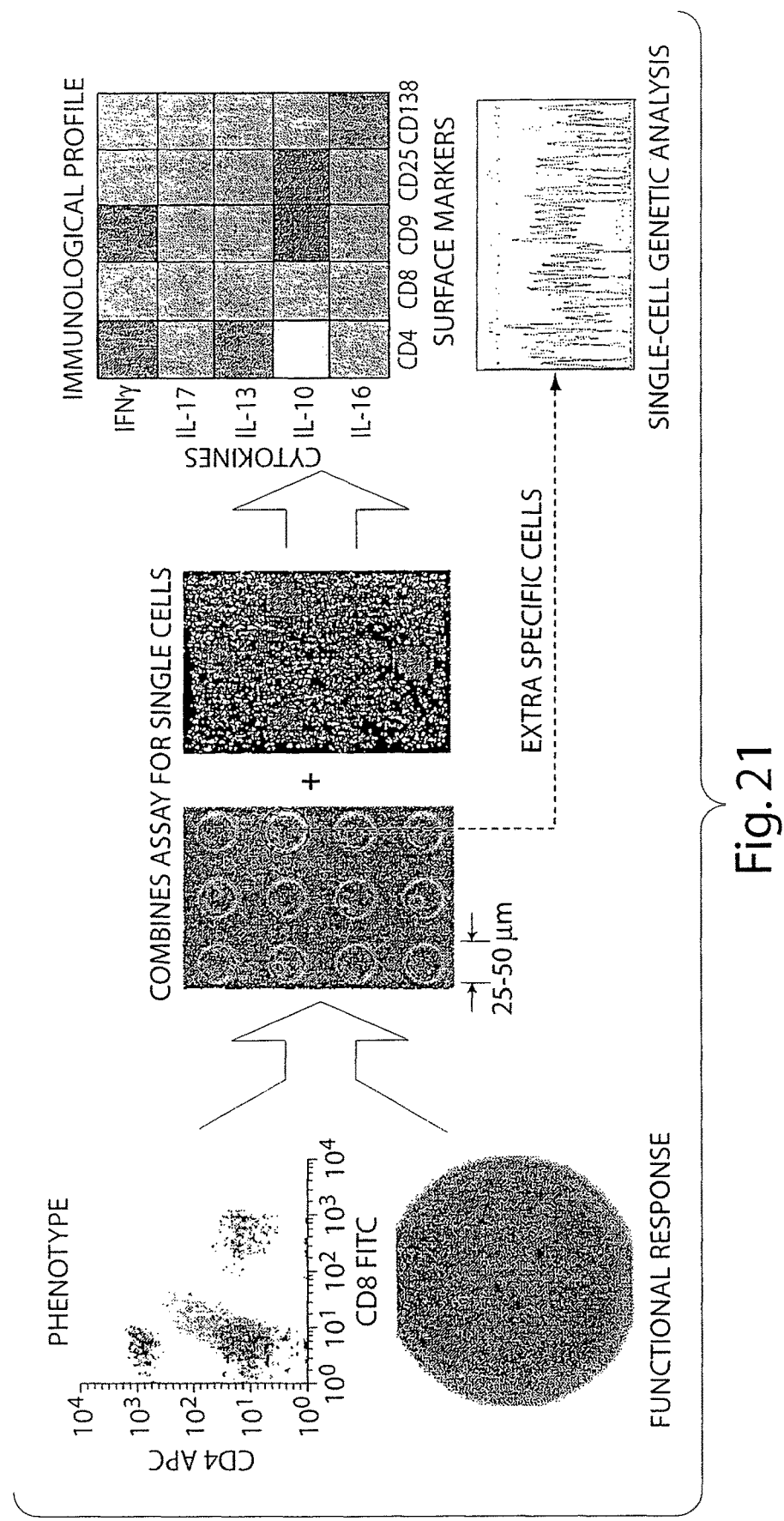
FIG. 21 is a drawing of a scheme for generating a single assay to measure both the phenotype and secretory function of individual cells.
Figure 22:
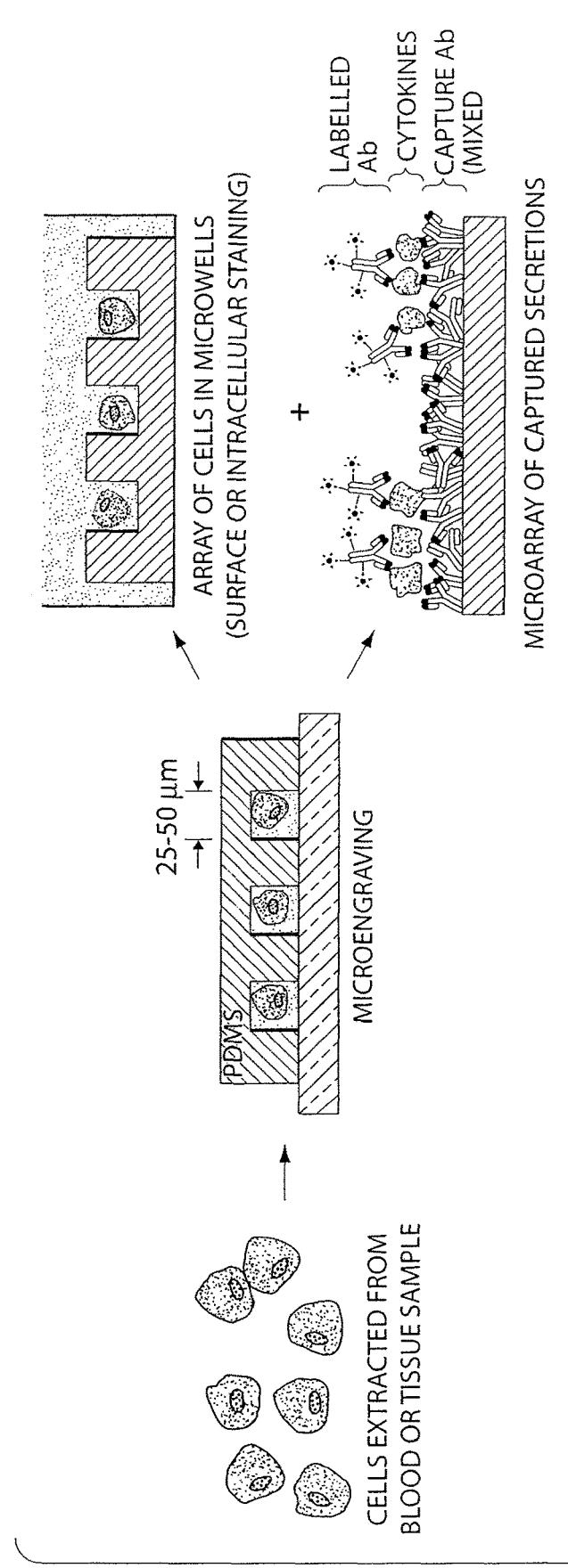
FIG. 22 is a drawing of a schematic diagram depicting the process for depositing cells from a suspension into microwells and capturing antibodies on a solid support.

Example 3: Simultaneous Determination of Phenotype and Functional Behavior of Individual Primary Cells Another application for the disclosed method, apparatus and kits is the determination of the phenotype of a cell and its functional behavior (e.g., secretion of extracellular factors) using soft lithography for measuring secreted factors from large numbers of single cells (>100,000) and for correlating them with the phenotypic markers displayed on the producing cell. Traditionally, these characteristics for cells extracted from tissue or blood are established by independent methods—for example, flow cytometry and immunosorbent assays—that provide information about either phenotype or function, but rarely both. Furthermore, existing methods for measuring functional behaviors, such as secretion of cytokines, often require additional manipulations and culturing to generate sufficient material from a bulk population of cells for detection. The graphical abstract (FIG. 21) suggests how a soft lithographic technique could provide both characteristics for a large number of cells. Comparison of the frequency of specific cells present after onset of a disease or administration of a vaccine would provide a profile of how an individual is responding relative to others. Extraction of specific cells by micromanipulation would allow genetic sequencing of unique markers (e.g., B cell or T cell receptors). Allowing a single assay to measure both the phenotype and secretory function of individual cells The method, apparatus and kits described may be extended for identifying and retrieving monoclonal hybridomas secreting antigen-specific antibodies so that a highly multiplexed platform for profiling large numbers (>100,000) of primary cells is generated on the basis of both secreted factors and surface markers (FIG. 22). Minimally, four unique secreted factors and phenotypic markers, are realized and detected with an aim to detect at least 10. The experiments described here establish the method using T and B cells from various tissues of mice, which can be extended to analyze human lymphocytes derived from blood samples.

Figure 23:
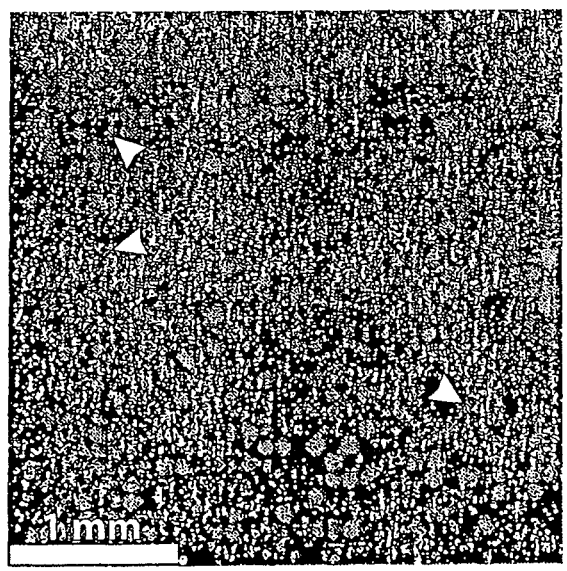
FIG. 23 is a fluorescent micrograph of an engraved microarray stained for captured IFNγ (green) and IL-4 (red, indicated with arrowheads).

The method described herein utilizes the microengraving method, apparatus and kits described, however, the immunosorbant capture of cytokines on the glass slide likely will require a sandwich-style format in which an antibody immobilized on the surface captures the factor of interest and a second antibody, reactive against a different epitope, is used for labeling. Though cytokines are typically secreted from cells at a rate that is 1000-fold less than that for antibodies produced by hybridomas or plasma cells, a single cell confined in a microwell of 50×50×50 µm$^3$ generates sufficient cytokines for a concentration of 25 ng/mL within 4 h. The nature of the assay requires immobilization of N different capture antibodies uniformly on the surface of the slide, where N is the number of secreted factors one aims to detect. This constraint may reduce the signal available from each secretion by a factor equal to the number of different cytokines probed. For two capture antibodies, the available surface area and reactive antibodies is sufficient for detection (FIG. 23). The composition of deposition buffers and testing alternative immobilization strategies can be altered to maximize the number of available sites for capture.

Multiplexed detection using fluorescent materials is limited by the number of emitted wavelengths that can be cleanly distinguished from one another. For traditional organic dyes and standard optical filters, the limit is approximately four. Two ways to extend this range are 1) the use of quantum dots as labels, and 2) spectral imaging (or deconvolution of overlapping signals). Quantum dots provide the optimal material for detecting a multitude of cytokines. Conjugated polyclonal, affinity-purified antibodies are directed against different cytokines to commercially-available quantum dots of various colors (Invitrogen or Evident Technologies) using N-hydroxylsuccinimide esters. Optimization of the labeling conditions and subsequent analysis of cross-reactivity is tested using spotted arrays of recombinant cytokines captured on glass slides slabing appropriate mixtures of capture antibodies. IFNγ (Th1 response), IL-2 (activated lymphocytes), IL-13 (Th2 response), and IL-10 (regulatory cells) are measured.

Both hybridomas and mononuclear cells from blood remain loosely adhered to the bottom surface of the poly (dimethylsiloxane) (PDMS) microwells during manipulations of the wells. Because the cells can remain in the wells, standard protocols are used for immunofluorescence to analyze extra- or intracellular proteins present on the cells. Scanning arrays of microwells containing labeled cells will require a microscope equipped with an automated stage and focus. Commercial instruments for laser-scanning cytometry on glass slides is suitable for the analysis, however, custom-designed optics can be tailored to allow the greatest degree of flexibility in analysis.

An exemplary analysis is carried out as follows. Cells, e.g., splenocytes from a mouse (e.g., C57Bl/6) are obtained and the number of cells with specific phenotypic markers and their secretion patterns determined by microengraving. For the evaluation of immune responses, the focus is initially on T cell markers (CD4 and CD8), and two chemokines (IFNγ and IL-13). FACS analysis provides confirmation of the frequency of cells. Intracellular staining for IFNγ and IL-13 gives an indication of the relative number of cells producing each of those cytokines. Splenocytes taken from transgenic OTII mice, which have CD4+ T cells expressing a T cell receptor specific for a peptide fragment derived from ovalbumin are used as an example. Immunization of these mice with ovalbumin, or cell cultures stimulated in vitro with the antigen and αIFNγ antibodies, skew the immune response to develop a Th1 or Th2 response.

The example experiment allows confirmation of a hypothesis suggested by Sallusto et al. that the age of a mature dendritic cell determines the likelihood of an interacting CD4+ T cell to polarize into Th1- or Th2-type. (Langenkamp, A., Messi, M., Lanzavecchia, A. & Sallusto, F. Kinetics of dendritic cell activation: impact on priming of TH1, TH2 and nonpolarized T cells. *Nat. Immunol.* 1, 311-316 (2000)). Dendritic cells from a donor mouse are isolated and exposed to ovalbumin in the presence of lipopolysaccharide for 8-48 h. After loading with antigen, the cells are transferred into an OTII mouse by intravenous tail injection. After 1-2 days, the frequency of Th1- and Th2-polarized T cells present in the lymph nodes and the spleen are measured as a function of the maturation time of the injected DCs. The DCs matured more than 12 h should induce a greater percentage of Th2-polarized or non-polarized T cells than DCs matured for less than 12 h.

The data demonstrated the development and verification of the technique for connecting phenotype with functional responses for large numbers of individual primary cells. The application of the technology is useful to profile immunological responses as a function of disease. It may be used in the context of transgenic mice with model diseases (diabetes, mouse pathogens), and to evaluate immune responses to human diseases, e.g., opportunistic fungal pathogens (e.g., *Aspergillus*), malaria, influenza, and diabetes using blood samples. Because the cells can be retrieved from the microwells by micromanipulation, the technique may be extended to include genetic sequencing of unique features from single cells identified in a screen, e.g., B cell or T cell receptors.

The application of the disclosed methods, apparatus, and kits will provide a tool for monitoring an immune response directly by determining the efficacy of a vaccine or correlating the frequencies of particular types of cells upon onset of a certain disease. The ability to use limited numbers of cells from a blood sample is particularly suited for use as a diagnostic tool to detect early genetic defects in pediatrics (e.g., immunodysregulation, polyendocrinopathy, and enteropathy, X-linked syndrome (IPEX)—a deficiency of CD4+CD25+ regulatory T cells). The relative ease of processing a sample by this method allows inexpensive diagnostic applications in clinical microlabs and/or third-world countries. The methods are useful to characterize cellular identity and behavior in patient-derived samples from individuals suffering from or at risk of developing infectious diseases, cancer, or neurological disorders.

Example 4: Engineering Antibodies to Improve their Orientation on Surfaces

To direct the orientation of cell secreted products relative to the surface on which they are printed, a nucleic acid sequence encoding a short peptide recognition sequence (5-15 residue, e.g., 8-10 residue sequence) is incorporated into a gene encoding the secreted polypeptide, e.g., the heavy and/or light chain of an immunoglobulin chain. An enzymatic or other chemical reaction installs a unique (orthogonal) chemical moiety on the short peptide sequence that would provide a specific site for attaching the secreted product, e.g., antibody, to a solid support or other scaffold (e.g., another molecule, enzyme, or polymer matrix). The enzyme inducing the conversion or chemical modification is encoded in the cell itself or is provided externally, e.g., extracellularly in the culture medium, A transgenic mouse carrying this modification is used to produce hybridomas containing this "chemical handle" without additional cloning or reengineering.

One example of such a peptide recognition sequence for a selected enzyme and the enzyme (BirA ligase). Another example is sortase, a transpeptidase encoded by many bacteria such as Staphylococcus aureus. Sortases recognize a 5-amino acid peptide motif, LPXTG (SEQ ID NO.: 3). Two other classes of enzymes that recognize short peptide motifs are transglutaminases and lipoic acid ligases. The modifications are made to either terminus of either the heavy or light chains, e.g., the the C-terminus of the heavy or light chains contains the chemical tag.

Figure 24:
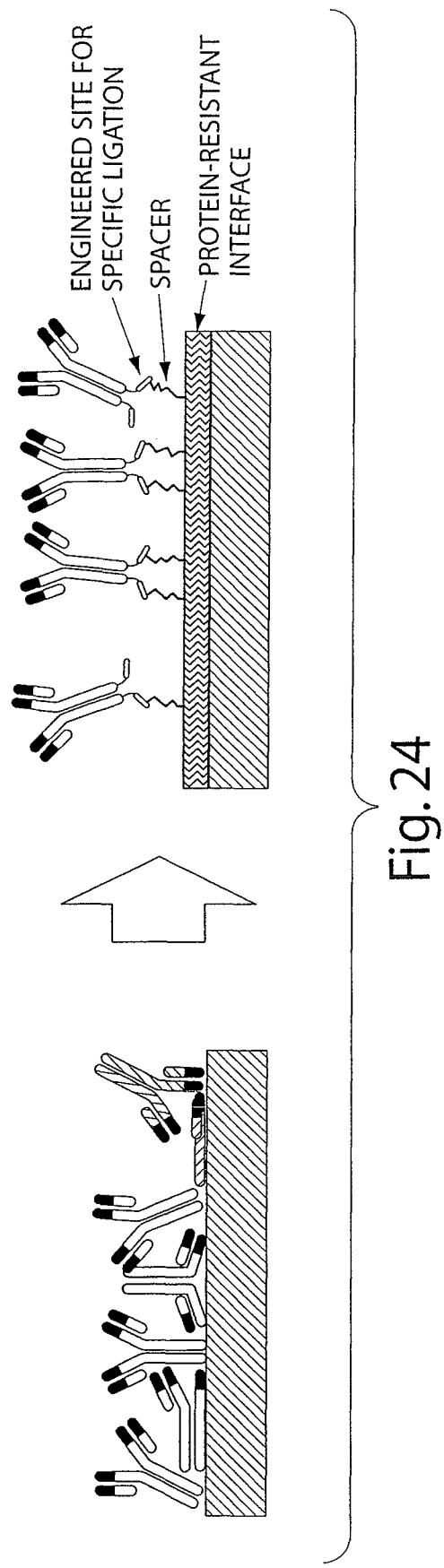
FIG. 24 is a drawing of a graphical abstract of antibodies engineered to allow enzymatic installation of a specific chemical moiety that can react with a functionalized organic surface designed to resist non-specific adsorption of proteins.

Immunoglobulins (Ig) are engineered to contain specific chemical sites for the purpose of improving orientation and accessibility of binding domains in surface-based and nanoparticle-based assays. Transgenic mice that contain the sequence encoding the sites for chemical modification are useful in making hybridomas that produce antibodies containing appropriate sites for defined ligation to surface-based assays or other molecular constructs (drugs, labels) without requiring additional cloning (FIG. 24).

Figure 25:
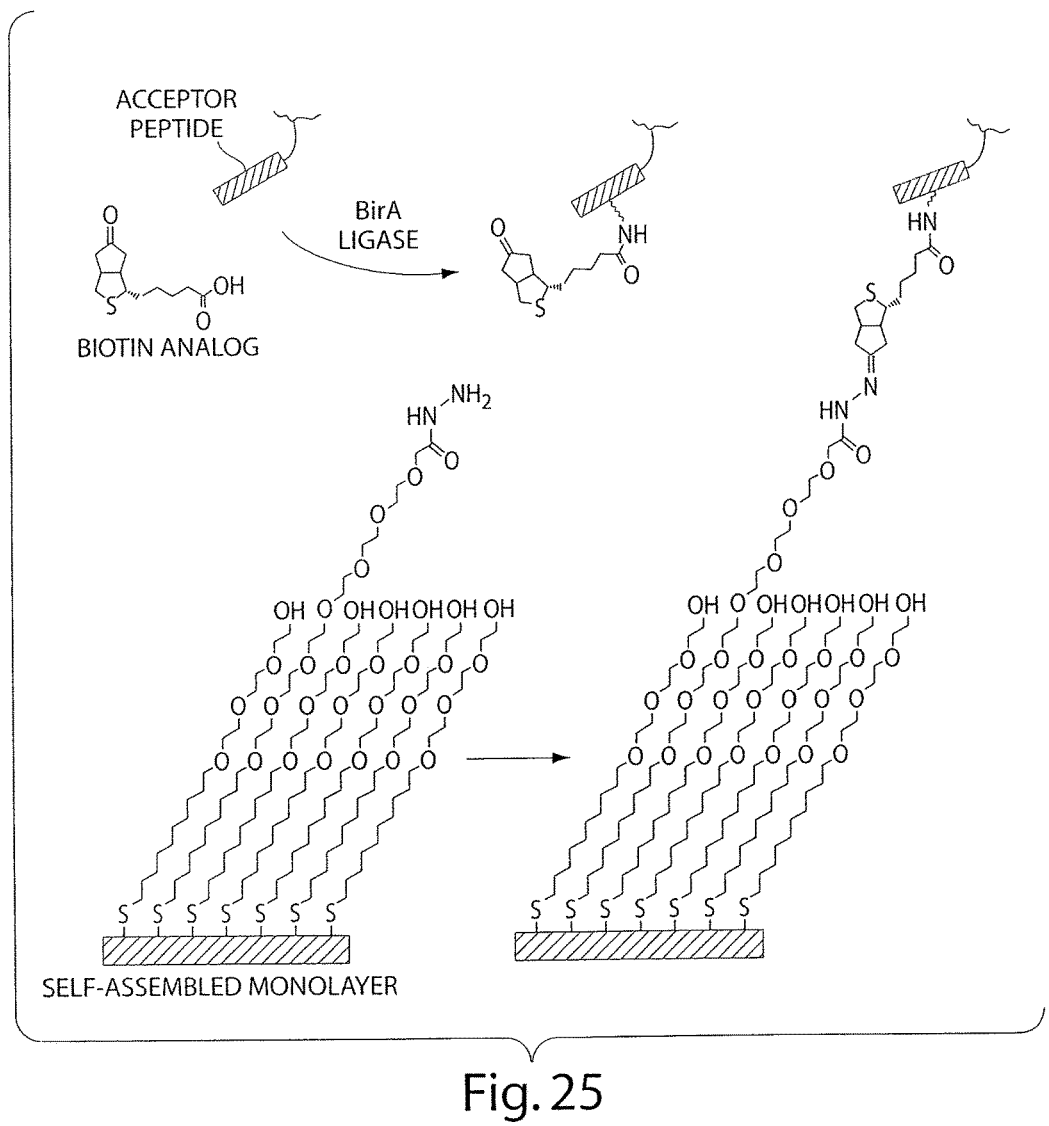
FIG. 25 is a drawing of a method for attaching antibodies modified with an analog of biotin to a SAM bearing a reactive hydrazide moiety.

The methods, apparatus and kits disclose a method for attaching antibodies to surfaces using a chemical functional group installed at the C-terminus of the heavy chain of an Ig-gamma (IgG) (FIG. 25). Attaching an antibody modified in this manner to a surface directs its orientation in a predictable manner, and thus improves functionality. For example, molecular cloning is used to insert a 15-amino acid peptide sequence (GLNDIFEAQKIEWHE (SEQ ID NO.: 4)) at the C-terminus of a secreted product such as an antibody. An enzyme, biotin ligase (BirA), produced by Escherichia coil ligates either biotin or a related ketone analog at the lysine residue in the peptide. Modification of the Ig heavy chain with the ketone analog will allow site-specific attachment using a hydrazide moiety present on the surface. This approach is used for immobilizing antibodies on self-assembled monolayers (SAMs) supported on gold or palladium.

A stably-transfected cell line, is generated that expresses an antibody with an appended amino-acid sequence at the C terminus of the heavy chain. The variable regions of the heavy and light chains (IgG1, κ) expressed by a mouse hybridoma, Hyb 9901 (anti-chicken ovalbumin), from mRNA are then cloned. These fragments are subcloned into mammalian expression vectors containing the constant regions for the heavy and light chains. At the 3' end of the sequence for the heavy chain a sequence encoding a 7 amino-acid epitope is inserted, which recognized by tobacco etch virus (TEV) protease (ENLYFQ/S (SEQ ID NO.: 5) where/indicates cleavage site) followed by the epitope recognized by the BirA ligase (GLNDIFEAQKIEWHE (SEQ ID NO.: 6)). Expression of the antibody is induced by transfection of the two plasmids into 293T or CHO cells. Proper assembly of secreted antibodies is verified by ELISA using immobilized ovalbumin.

BirA ligase from E. coli cultures is expressed and purified and then an analog of biotin containing a ketone is synthesized according to reported protocols. To ligate the analog to the modified antibodies collected from the cell cultures, a buffered solution of the antibodies is incubated with BirA, biotin analog, and ATP. Successful modification of the antibodies is confirmed by Western blot analysis using anti-mouse IgG to identify the heavy chain and anti-biotin antibodies (or streptavidin).

SAMs are prepared on thin films (20 nm) of gold or palladium using a mixture of two thiols, (1-Mercapto-11-undecyl) tri(ethylene glycol) and a hydrazide-terminated derivative, $HS(CH_2)_{11}(OCH_2CH_2)_6OCH_2CO_2NHNH_2$. The density of sites for attachment are controlled by varying the molar ratio of the two thiols used to prepare the SAM. Exposure of the surface to a buffered solution of the modified antibodies will lead to ligation (FIG. 25). The relative density of functional antibodies immobilized on the SAMs is measured by surface plasmon resonance using SAMs with antibodies immobilized by standard protein coupling methods (e.g., EDC-NHS ester) as controls.

The example described here establishes a method for attaching antibodies to surfaces using a specific chemical ligation at the C-terminus of the heavy chain, Using this example, the modification of gold nanoparticles or quantum dots with the engineered antibodies may be conducted. A transgenic mouse incorporating the peptide tail at the C terminus of the IgG1 constant region is generated. Thus, all IgG1 antibodies generated by hybridomas from these mice incorporate the specific handle for oriented attachment without additional cloning or modifications. Such antibodies would have an intrinsic site for subsequent modifications (orthogonal labeling, monovalent ligation of a drug or enzyme).

When introducing elements of the examples disclosed herein, the articles "a," "an," "the" and "said" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples. Should the meaning of the terms of any of the patents or publications incorporated herein by reference conflict with the meaning of the terms used in this disclosure, the meaning of the terms in this disclosure are intended to be controlling.

Although certain aspects, examples and embodiments have been described above, it will be recognized by the person of ordinary skill in the art, given the benefit of this disclosure, that additions, substitutions, modifications, and alterations of the disclosed illustrative features, aspects, examples and embodiments are possible.

What is claimed:

1. An apparatus comprising a moldable slab in contact with a substrate, said moldable slab defining a plurality of wells, wherein each well has a side or diameter of less than 100 microns and contains not more than a single or a few cell(s), wherein at least one of said wells contains the respective single or few cell(s), said respective single or few cell(s) having produced one or more cell-derived product(s) in a volume no greater than about 10 nanoliters in each said well containing said respective single or few cell(s), said one or more cell-derived product(s) being bound to the substrate at a location in fluid communication with said respective well containing said respective single or few cell(s).

2. The apparatus of claim 1, wherein each well has a diameter of 10 to 100 microns.

3. The apparatus of claim 2, wherein each well has a diameter of 50 to 100 microns.

4. The apparatus of claim 1, wherein the respective single or few cell(s) produce the cell-derived product in a volume of 100 picoliters to 1 nanoliter.

5. The apparatus of claim 1, wherein the substrate is a glass substrate.

6. The apparatus of claim 1, wherein the moldable slab comprises poly(dimethylsiloxane).

7. The apparatus of claim 1, wherein the respective single or few cell(s) comprise(s) one or more members selected from the group consisting of a T cells, a B cells, a liver cells, and a kidney cells.

8. The apparatus of claim 1, wherein the cell-derived product comprise(s) one or more members selected from the group consisting of a DNA, RNA, cytokine, chemokine, inflammatory mediator, monokine, lymphokine, a growth factor, a lipid, and a pathogen.

9. The apparatus of claim 1, wherein the moldable slab is reversibly sealed to the substrate so as to form a substantially fluid tight seal.

10. The apparatus of claim 1, wherein each well has a diameter of 10 to 100 microns;
    the respective single or few cell(s) produce the cell-derived product in a volume of 100 picoliters to 1 nanoliter;
    the substrate is a glass substrate;
    the moldable slab comprises poly(dimethylsiloxane); and
    the moldable slab is reversibly sealed to the substrate so as to form a substantially fluid tight seal.

11. The apparatus of claim 1, wherein the substrate comprises a plastic material.

12. The apparatus of claim 1, wherein the cell-derived product(s) is/are secreted.

13. The apparatus of claim 1, wherein the cell-derived product(s) is/are liberated from the respective single or few cell(s) by lysis or permeabilization.

14. The apparatus of claim 1, wherein the substrate has a capture ligand immobilized thereon for retaining at least one of the cell-derived product(s), wherein the capture ligand is an antigen, a protein or an antibody.

15. The apparatus of claim 1, wherein the substrate has a substantially planar surface.

16. A method comprising temporarily confining cells in a plurality of wells using the apparatus of claim 1, and selectively recovering the single or few cell(s) from an identified well, said well identified from the one or more cell-derived product(s) produced by said single or few cell(s) while temporarily confined in said well, said one or more cell-derived product(s) being bound to the substrate at a location having been in fluid communication with said well.

\* \* \* \* \*

UNITED STATES PATENT AND TRADEMARK OFFICE
CERTIFICATE OF CORRECTION

PATENT NO.         : 11,154,833 B2
APPLICATION NO.    : 16/170323
DATED              : October 26, 2021
INVENTOR(S)        : J. Christopher Love et al.

Page 1 of 1

It is certified that error appears in the above-identified patent and that said Letters Patent is hereby corrected as shown below:

In the Claims

Column 37, Claim 4, Line 27, please delete "product" and insert --product(s)--.

Column 37, Claim 7, Line 35-36, please delete "a T cells, a B cells, a liver cells, and a kidney cells" and insert --a T cell, a B cell, a liver cell, and a kidney cell--.

Column 37, Claim 8, Line 37, please delete "product" and insert --product(s)--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 8
<212> TYPE: PRT

```
<213> ORGANISM: Artificial Sequence
<220> FEATURE:
<223> OTHER INFORMATION: Chemically Synthesized

<400> SEQUENCE: 1

Ser Ile Ile Asn Phe Glu Lys Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 2

Ser Ile Tyr Arg Tyr Tyr Gly Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Leu Pro Xaa Thr Gly
1               5

<210> SEQ ID NO 4
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 4

Gly Leu Asn Asp Ile Phe Glu Ala Gln Lys Ile Glu Trp His Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (6)..(7)
<223> OTHER INFORMATION: Cleavage site between amino acids at location 6
      and 7

<400> SEQUENCE: 5

Glu Asn Leu Tyr Phe Gln Ser
1               5

<210> SEQ ID NO 6
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 6
```

```
Gly Leu Asn Asp Ile Phe Glu Ala Gln Lys Ile Glu Trp His Glu
1               5                   10                  15
```